(12) United States Patent
Costanzo

(10) Patent No.: US 7,703,486 B2
(45) Date of Patent: Apr. 27, 2010

(54) METHOD AND APPARATUS FOR THE HANDLING OF A RADIOPHARMACEUTICAL FLUID

(75) Inventor: Jerry Costanzo, Loomis, CA (US)

(73) Assignee: Cardinal Health 414, Inc., Dublin, OH (US)

( * ) Notice: Subject to any disclaimer, the term of this patent is extended or adjusted under 35 U.S.C. 154(b) by 854 days.

(21) Appl. No.: 11/447,557

(22) Filed: Jun. 6, 2006

(65) Prior Publication Data

US 2007/0289668 A1   Dec. 20, 2007

(51) Int. Cl.
*B65B 1/04* (2006.01)

(52) U.S. Cl. .................... 141/346; 141/2; 141/320; 141/329; 604/416

(58) Field of Classification Search .............. 141/2, 141/319–323, 329, 330, 346; 604/403–416
See application file for complete search history.

(56) References Cited

U.S. PATENT DOCUMENTS

| | | | | |
|---|---|---|---|---|
| 5,492,147 A | * | 2/1996 | Challender et al. | 137/614.05 |
| 5,526,853 A | * | 6/1996 | McPhee et al. | 141/329 |
| 5,607,392 A | * | 3/1997 | Kanner | 604/86 |
| 6,183,465 B1 | * | 2/2001 | Meier et al. | 604/535 |
| 6,253,804 B1 | * | 7/2001 | Safabash | 141/97 |
| 7,080,672 B2 | * | 7/2006 | Fournie et al. | 141/383 |
| 7,128,105 B2 | * | 10/2006 | Tribble et al. | 141/319 |

* cited by examiner

*Primary Examiner*—Timothy L Maust
(74) *Attorney, Agent, or Firm*—Dicke, Billig & Czaja, PLLC

(57) ABSTRACT

An apparatus for the handling of hazardous fluids includes a collection vessel, a collection vessel connector, a dose control connector, a unit dose container, a delivery control connector, and a delivery site access device. The collection vessel contains the fluid prior to dispensing, the unit dose container contains a predetermined amount of the fluid for dispensing, the delivery site access device provides access to an intended delivery site, and the connector attaches pieces of the apparatus to one another. The method of the invention allows needle-free connections to be made for the apparatus, using a predetermined arrangement of the pieces of the apparatus, and in one embodiment, employs deformable elastomeric valves capable of creating a decreased pressure at a valve surface, so that upon closure of said valves, a fluid on the surface on the valves is withdrawn within the connector.

35 Claims, 16 Drawing Sheets

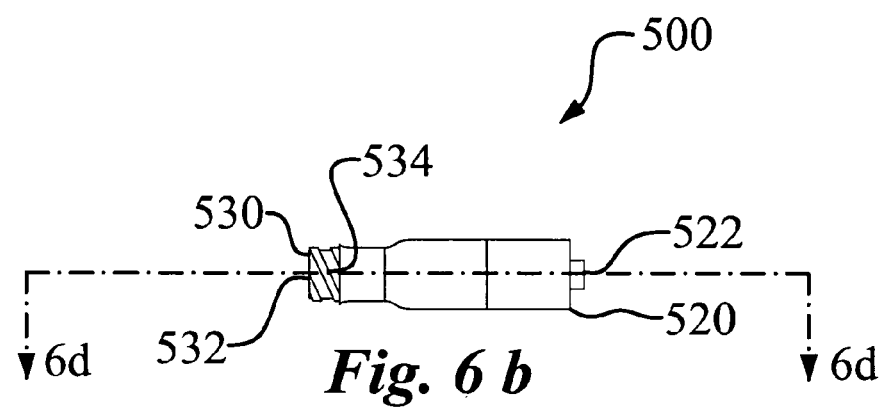
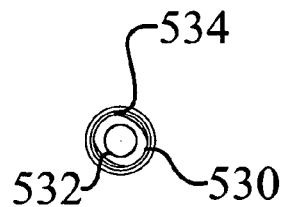
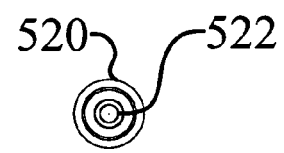

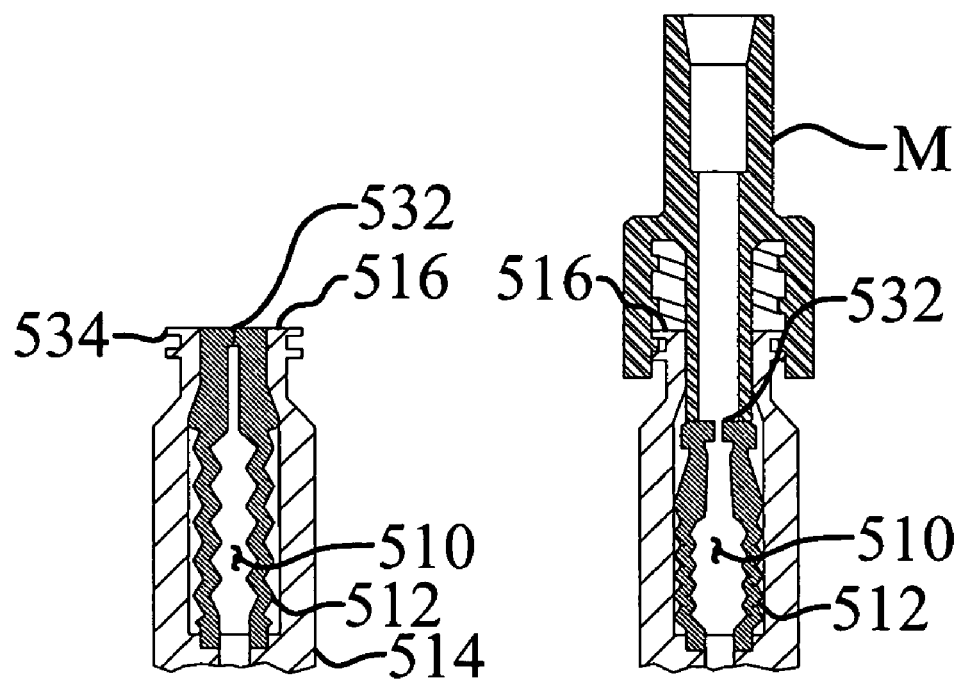
*Fig. 6d*  *Fig. 6e*

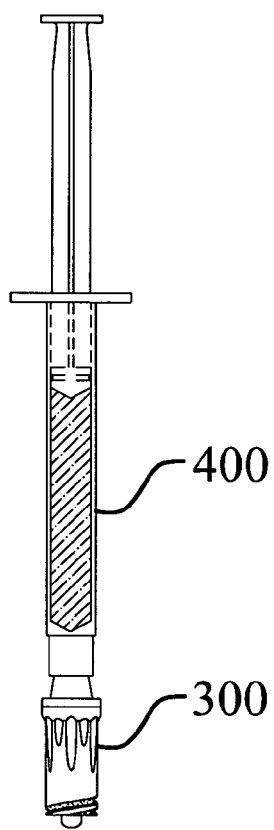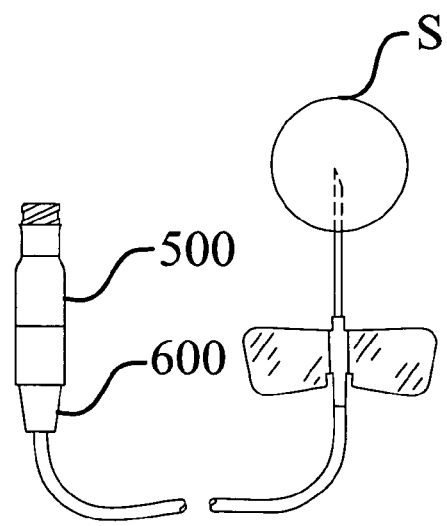
*Fig. 13 a*   *Fig. 13 b*

METHOD AND APPARATUS FOR THE HANDLING OF A RADIOPHARMACEUTICAL FLUID

TECHNICAL FIELD

The present invention relates to a method and apparatus for the handling of a hazardous fluid, particularly hazardous injectable medicaments, utilizing self sealing interlocks to contain the hazardous fluid during the process of dispensing, transportation, and administration of such fluids.

BACKGROUND OF THE INVENTION

The dispensing and transportation of hazardous fluids, particularly hazardous injectable medicaments, has many complexities. On its simplest level, a needle and syringe combination is typically used to withdraw injectable medicament from a storage container, the needle is capped, and then the syringe is transported to the injection site. The storage container is most often sealed with a pierceable septum formed of an elastomeric material such as latex rubber or the like, captured in an access port. A sharp needle is inserted into the access port piercing the septum to position the distal, open end of the cannula past the septum to make fluid connection with the interior of the access port. Upon withdrawal of the sharp cannula, the elastomeric septum reseals itself, thus maintaining a sterile environment within the storage container. The outer surface of the septum of the injection site is wiped with an antiseptic before each use to prevent septic agents from being drawn into the access port by the piercing movement of the needle.

A similar process may be used to inject the medicament into an intravenous catheter inserted into the vein of a patient, or into a connector in an intravenous fluid line attached to such an intravenous catheter.

However, this simple system particularly fails in the safe handling of hazardous injectable medicaments. Firstly, while it is always dangerous to dispense fluid through sharp needles, because of the dangers of accidental needle stick of medical personnel and the attendant risks of transmitting blood borne diseases, this is particularly true when the injectable medicament is itself a hazardous substance. Such substances include, by way of example only, chemotherapeutic agents and radionuclide agents commonly used for medical imaging purposes. In such cases, accidental needle sticks pose the additional risk of exposure to highly dangerous substances.

Secondly, the traditional needle tipped syringe is not hermetically sealed to contain fluids, at best generally depending on the frictional fit of a syringe barrel and a needle cap to contain liquids. A capped needle is prone to leakage, and syringes containing hazardous agents are apt to leave a trail of contamination behind them during transport. This particularly acute in the transport of radioactive medicaments that are traditionally transported to an intended site of use in a shielded metal transportation vessels, often known as "pigs." Any leak during transport, even of a minute amount of radioactive material, contaminates the interior surface of the "pig," which then poses risks to unsuspecting handlers until the "pig" undergoes a painstaking decontamination before it may be reused. Attempts have been made, such as that seen in U.S. Pat. No. 5,180,542 to Brown, to design transport containers that try to contains spills, but a more productive approach would be to prevent contamination in the first place.

Many attempts have been made to increase the safety of administering medicaments through needle and syringe combinations. For example, U.S. Pat. No 6,537,257 to Wien is typical of the approach of trying to guard the sharp needle tip to decrease the chance of accidental needle sticks. Often, these take the form of having retractable guards, as seen in U.S. Pat. No. 6,921,382 to Lee et al. Handling of needle tipped syringes containing hazardous fluid may be minimized with devices such as that seen in U.S. Pat. No. 4,638,809 to Kuperus, where a radionuclide is reconstituted from a lyophilized preparation within the administering syringe, thus halving the number of manipulations that must be made with a typical needle-tipped syringe. However, the risk of needle related accidents, while perhaps attenuated, will remain with all these inventions, and for as long as a needle is part of the apparatus.

Finally, the system of using needles and syringes to dispense, transport, and administer hazardous agents suffers from the dangerous drawback of being "universal" in their access to medical appliances. Since all medical injection needles and elastomeric septum sealed connectors operate in an essentially identical manner, syringes containing hazardous agents may be attached to a large number of injection sites, including patients for whom these hazardous substances are not intended. Furthermore, since essentially all hypodermic needles and syringes in common use interconnect in the same manner and with the same size connectors, commonly know in the art as "Luer lock" connections, there are currently no points in the storage, transport, or administration cycle where hazardous vessels may be isolated from use in everyday intravenous access equipment. In short, there is nothing to prevent a dangerous radionuclide or chemotherapeutic agent from being mistakenly injected into the intravenous tubing of a patient who is not supposed to receive it. The instant invention of a method and apparatus for the handling of hazardous fluids solves these problems utilizing unique series of self-sealing elastomeric interlocking connectors.

SUMMARY OF THE INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations. The instant invention demonstrates such capabilities and overcomes many of the shortcomings of prior methods in new and novel ways.

The instant invention is an apparatus and method for handling a hazardous fluid.

The apparatus consists generally of a collection vessel, a collection vessel connector, a dose control connector, a unit dose container, a delivery control connector, and a delivery site access device. The collection vessel may be used to enclose a hazardous fluid, and is sealed from the environment, in one embodiment, by an elastomeric closure, which may also include a puncturable resealable elastomeric seal. The connectors are used to connect pieces of the apparatus in a predetermined manner, and employ deformable elastomeric valves to reversibly seal internal channels which provide fluid communication between the pieces of the apparatus. A unit dose container is used to contain a unit dose of the hazardous fluid. A delivery site access device is used to place assembled pieces of the apparatus in fluid communication with an intended delivery site.

A particular type of elastomeric valve closure, as taught by Leinsing in U.S. Pat. No. 6,142,446, may be useful as part of an embodiment of the apparatus. The important aspect of such valves is that they close prior to the closure of the inventive closed male connector.

An effect of the disconnection of the inventive closed male connector valve and the concomitant increase of the internal volume of the valve is that a decreased pressure is created at the fluid port as the valve is closing. This creates a tendency for a fluid on the surface of the fluid port to be drawn back into the internal channel, rather than being left on the surface of the fluid port. Thus, in such an embodiment, the instant invention not only increases safety by eliminating needles or other sharp objects from the apparatus, but increases safety in that fluid left on the fluid ports of the apparatus is drawn back into the inventive closed male connector rather than being left behind on the surface to contaminate the environment.

In a common embodiment, the potentially interlocking mating pairs of connectors enumerated above may be formed using standard sized and designed connectors such as would be known to one skilled in the art, and as are commonly called "Luer lock" connectors. Such an embodiment has the advantage of making the apparatus compatible with standard syringes and intravenous tubing. However, as a safety and security measure, it may be desirable to configure the potentially interlocking pairs of connectors using a unique interlock safety feature. Such interlock safety features could encompass color coding, non-standard interlock shape or sizing, reverse threads on the interlocks, or a unique mating key system. This would present a unique safety check such that potentially dangerous materials could only be administered using a complete and compatible system of apparatus.

In another embodiment, the collection vessel connector female end fluid port interlock, the dose control connector female end fluid port interlock, delivery control connector female end fluid port interlock, and the delivery site access device female end fluid port interlock all further comprise a common interlock safety feature that is capable only of mating with a reciprocally common interlock safety feature, found on the dose control connector fluid port interlock, the delivery control connector male end fluid port interlock, and the unit dose connector fluid port interlock, respectively.

Such embodiments would necessarily present several advantages. Any person handling the apparatus would be aware, by virtue of its non-standard interlock safety features, that this is a special apparatus requiring special handling. It would be very difficult to inject a substance contained in the apparatus to a patient with a standard delivery site access device, such as routinely found in standard intravenous tubing. Thus, by controlling caregiver access to certain portions of the apparatus to the specially trained, safety and accountability are increased.

The apparatus may also be configured in such a manner that one or more of the pieces of apparatus are permanently, rather than releasably, attached to one another. This has the advantage of decreasing the total number of parts, decreasing the complexity of certain of the parts, and increasing the likelihood that pieces of the apparatus will not be interchangeable with standard fluid handling devices, thereby increasing safety.

The instant invention also includes a method for the handling of a hazardous fluid. Such a method may be described as being performed both by a "preparer" and an "administrator," although one skilled in the art will realize such roles as exemplary only and may, in fact, be accomplished by one person.

Such a method includes a preparer first enclosing a collection vessel volume of a hazardous fluid in a collection vessel. Next, the preparer releasably interlocks the collection vessel connector to the collection vessel. The preparer then releasably interlocks the unit dose container to the dose control connector and releasably interlocks the dose control connector to the collection vessel connector. There is a unit dose container fluid manipulation regulator that regulates the unit dose container volume.

The preparer then withdraws a predetermined amount of a hazardous fluid from the collection vessel through the collection vessel connector, thence through the dose control connector, and thence into the unit dose container by manipulation of the unit dose container fluid manipulation regulator.

The preparer next releasably detaches the dose control connector from the collection vessel connector. The preparer, or some other person, then suitably transports the connected dose control connector and unit dose container to a point of use; whereupon the method will be employed by a person, called, by way of example only, the "administrator."

The administrator first releasably attaches a delivery site access device to a delivery site. By way of example, and not limitation, a delivery site may be the lumen of a blood vessel. The administrator then releasably interlocks a delivery control connector to the delivery site access device, and then releasably interlocks the dose control connector to the delivery site access device. The administrator may then dispense the hazardous fluid from the unit dose container through the dose control connector, thence through the delivery control connector, and thence through the delivery site access device to the delivery site, by means of manipulating the unit dose container fluid manipulation regulator.

Next, the administrator releasably detaches the dose control connector from the delivery control connector. In suitable embodiments using appropriate connectors, the method may be practiced such that the step of disengaging the dose control connector and the collection vessel connector thereby creates a decreased pressure withdrawing a fluid remaining on a surface of the collection vessel connector female end fluid port into the collection vessel connector. Similarly, the disengaging of the dose control connector and the delivery control connector thereby may cause a decreased pressure withdrawing a fluid on the surface on a surface of the delivery control connector female end fluid port into the delivery control connector.

After detachment, the administrator, or another person, removes the connected dose control connector and unit dose container from the point of use and suitably transports the connected dose control connector and unit dose container to a point of disposal. Disposal of the apparatus may be completed by removing the connected delivery site access device and delivery control connector from the delivery site and suitably transporting the connected delivery site access device and delivery control connector to a point of disposal.

At the point or points of disposal, personnel then suitably dispose of the dose control connector, the unit dose container, the delivery control connector, and the delivery site access device. It will be obvious to one skilled in the art that the pairs of apparatus comprising (a) the connected dose control connector and unit dose container; and (b) the connected delivery site access device and delivery control connector, will not generally need to be separated for disposal, thus minimizing the opportunities for contamination of the environment, or of workers.

The method may be practiced in a large number of embodiments. For example, in one embodiment, the act of releasably interlocking the collection vessel connector to the collection vessel may further comprise puncturing a collection vessel connector male end fluid port ingress means through a collection vessel fluid port puncturable resealable elastomeric seal in order to place the collection vessel male end fluid port in fluid communication with the collection vessel volume.

Furthermore, the method may include suitably transporting the connected dose control connector and unit dose container to a point of use in a closed container having an adsorbent inner layer and a moisture resistant outer layer, so that any leakage will be adsorbed by the inner layer for easy and safe disposal. For particular substances, such as by way of example only, radionuclides, suitably transporting the connected dose control connector and unit dose container to a point of use further may comprise enclosing the connected dose control connector and unit dose container in a radiation shielded container. Obviously, return of the apparatus to a point of disposal could be made using the same type of containers and precautions as are used for transporting of the apparatus to the intended point of use.

The instant invention may also be practiced in embodiments in which one or more of the pieces of the apparatus are permanently, rather than releasably attached. This includes embodiments where one, or both, of the pairs of (a) the dose control connector and the unit dose container; and/or (b) the delivery control connector and the delivery site access device; are permanently attached. Such a method obviates the need for assembling a dose control connector and a unit dose container; and a delivery control connector and a delivery site access device; and may reduce both the number and complexity, of elastomeric closures required in the apparatus.

These variations, modifications, alternatives, and alterations of the various preferred embodiments, arrangements, and configurations may be used alone or in combination with one another as will become more readily apparent to those with skill in the art, with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

FIG. 6a is a top plan view of an embodiment of a delivery control connector (500) of the instant invention, not to scale;

FIG. 6b is a side elevation view of an embodiment of a delivery control connector (500) of the instant invention, not to scale;

FIG. 6c is bottom plan view of an embodiment of a delivery control connector (500) of the instant invention, not to scale;

FIG. 6d is a partial section view of a prior art embodiment of a delivery control connector (500), taken along the section line 6d-6d of FIG. 6b, showing the delivery control connector internal channel elastomeric valve female end (516) in the sealed (valve closed) position, not to scale;

FIG. 6e is a partial section view of a prior art embodiment of a delivery control connector (500), taken along the section line 6d-6d of FIG. 6b, showing the delivery control connector internal channel elastomeric valve female end (516) in the open (valve opened) position, not to scale;

DETAILED DESCRIPTION OF THE INVENTION

The method and apparatus for the handling of hazardous fluids of the instant invention enables a significant advance in the state of the art. The preferred embodiments of the apparatus accomplish this by new and novel arrangements of elements that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Referring generally to FIGS. 1 through 13, the instant invention includes a method and an apparatus (10) for the handling of a hazardous fluid. In a suitable preparation area, including but not limited to a pharmacy, a preparer assembles the following apparatus (10).

Figure 1:
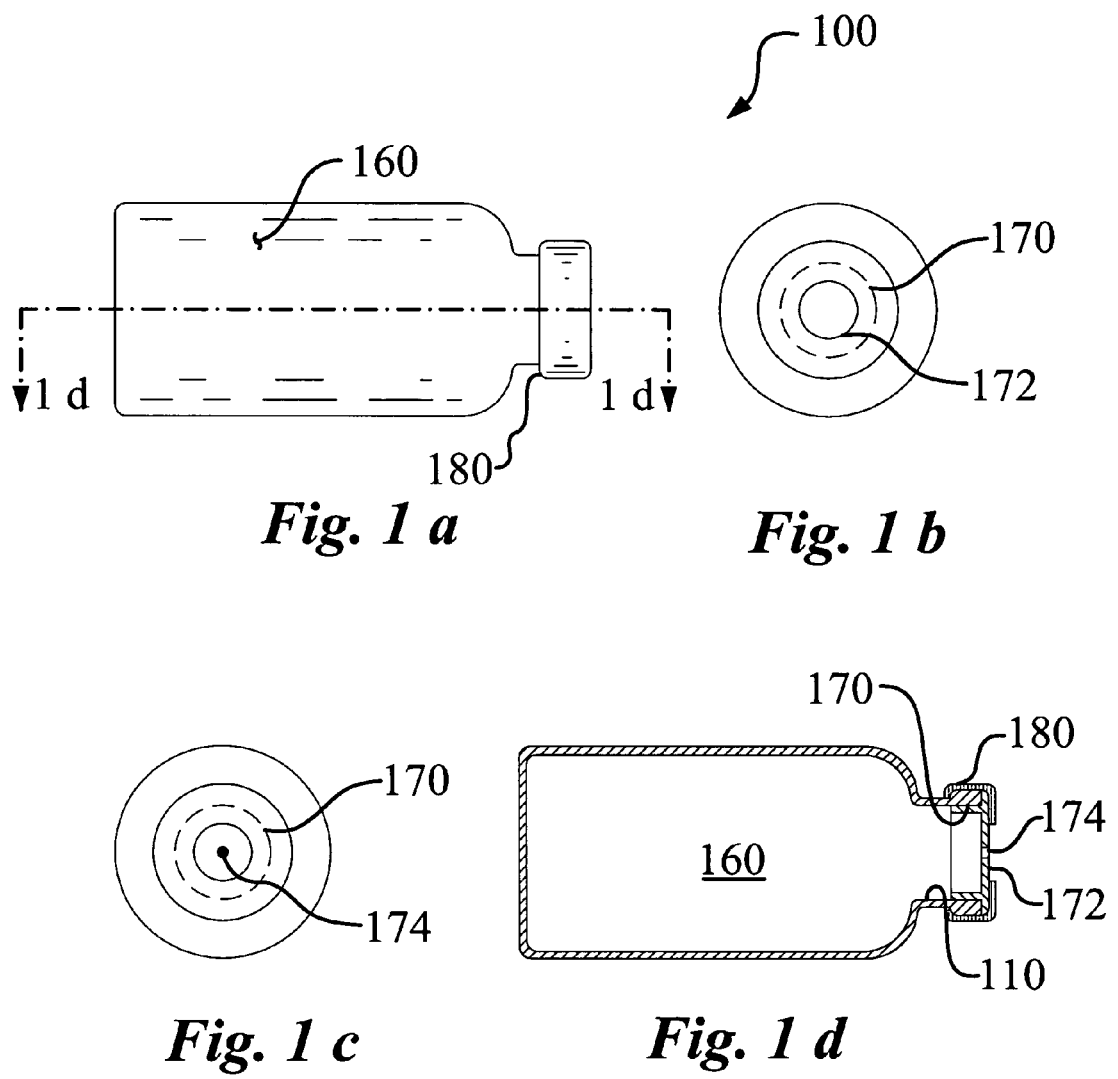
FIG. 1a is a side elevation view of an embodiment of a collection vessel (100) of the instant invention, not to scale.
FIG. 1b is a top plan view of an embodiment of a collection vessel (100) of the instant invention, not to scale.
FIG. 1c is a top plan view of another embodiment of a collection vessel (100) of the instant invention, not to scale.
FIG. 1d is a section view of an embodiment of a collection vessel (100) of the instant invention, taken along section line 1d-1d seen in FIG. 1a, not to scale.
Figure 2:
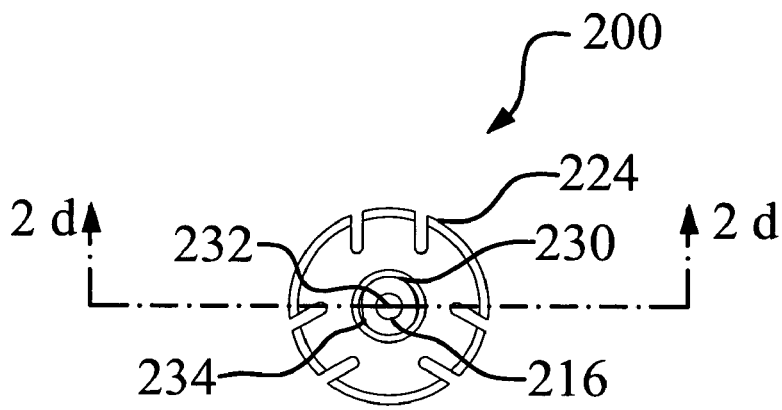
FIG. 2a is a top plan view of a an embodiment of a collection vessel connector (200) of the instant invention, not to scale.
FIG. 2b is a side elevation view of an embodiment of a collection vessel connector (200) of the instant invention, not to scale.
FIG. 2c is a bottom plan view of an embodiment of a collection vessel connector (200) of the instant invention, not to scale.
FIG. 2d is a section view of an embodiment of the collection vessel connector (200) taken along the section line 2d-2d seen in FIG. 2a, not to scale.
Figure 2:
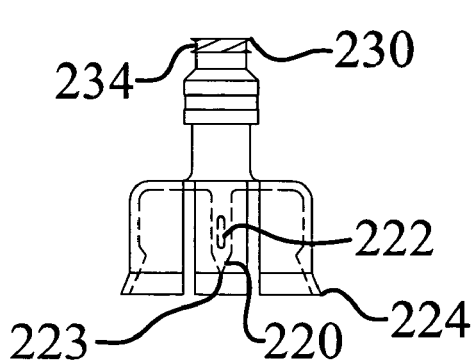
Figure 2:
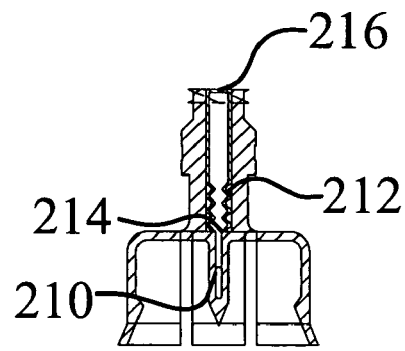
Figure 2:
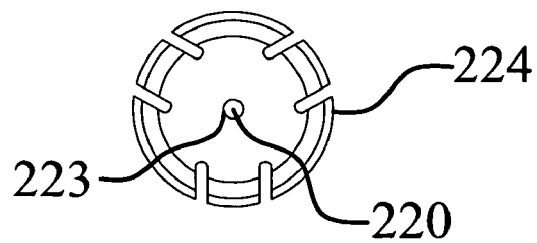
Figure 3:
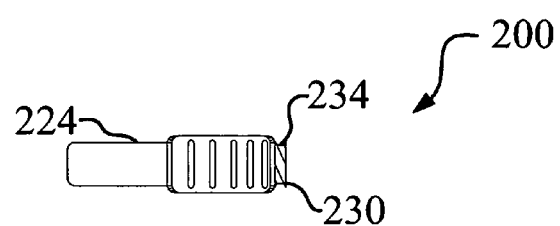
FIG. 3a is a side elevation view of another embodiment of a collection vessel connector (200) of the instant invention, not to scale.
FIG. 3b is a top plan view of another embodiment of a collection vessel connector (200) of the instant invention, not to scale.
FIG. 3c is a side elevation view of another embodiment of a collection vessel connector (200) of the instant invention, not to scale.
FIG. 3d is a bottom plan view of another embodiment of a collection vessel connector (200) of the instant invention, not to scale.
Figure 3:
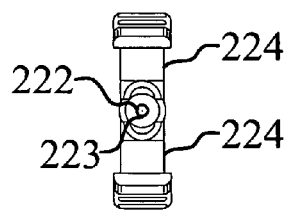
Figure 3:
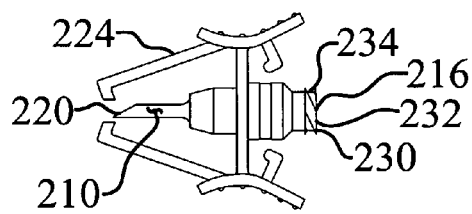
Figure 3:
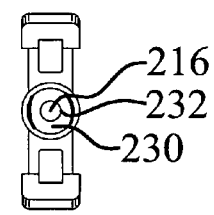
Figure 4:
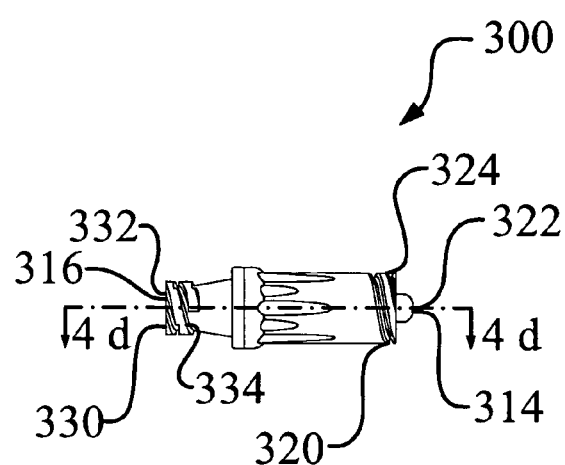
FIG. 4a is a top plan view of an embodiment of a dose control connector (300) of the instant invention, not to scale.
FIG. 4b is a side elevation view of an embodiment of a dose control connector (300) of the instant invention, not to scale.
FIG. 4c is a bottom plan view of an embodiment of a dose control connector (300) of the instant invention, not to scale.
FIG. 4d is a section view of a prior art embodiment of a dose control connector (300), taken along section line 4d-4d seen in FIG. 4b, showing the dose control connector internal channel deformable elastomeric valve male end (314) in the sealed (valve closed) position, not to scale.
FIG. 4e is a section view of a prior art embodiment of a dose control connector (300) of the instant invention take along section line 4d-4d of FIG. 4b, showing the dose control connector internal channel deformable elastomeric valve male end (314) in the unsealed (valve open) position, with indication of the fluid path through the open valve, not to scale.
Figure 4:
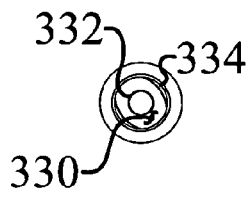
Figure 4:
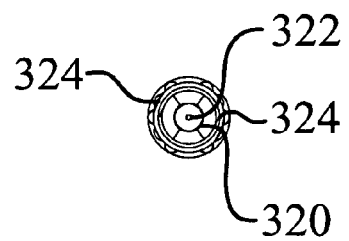
Figure 4D:
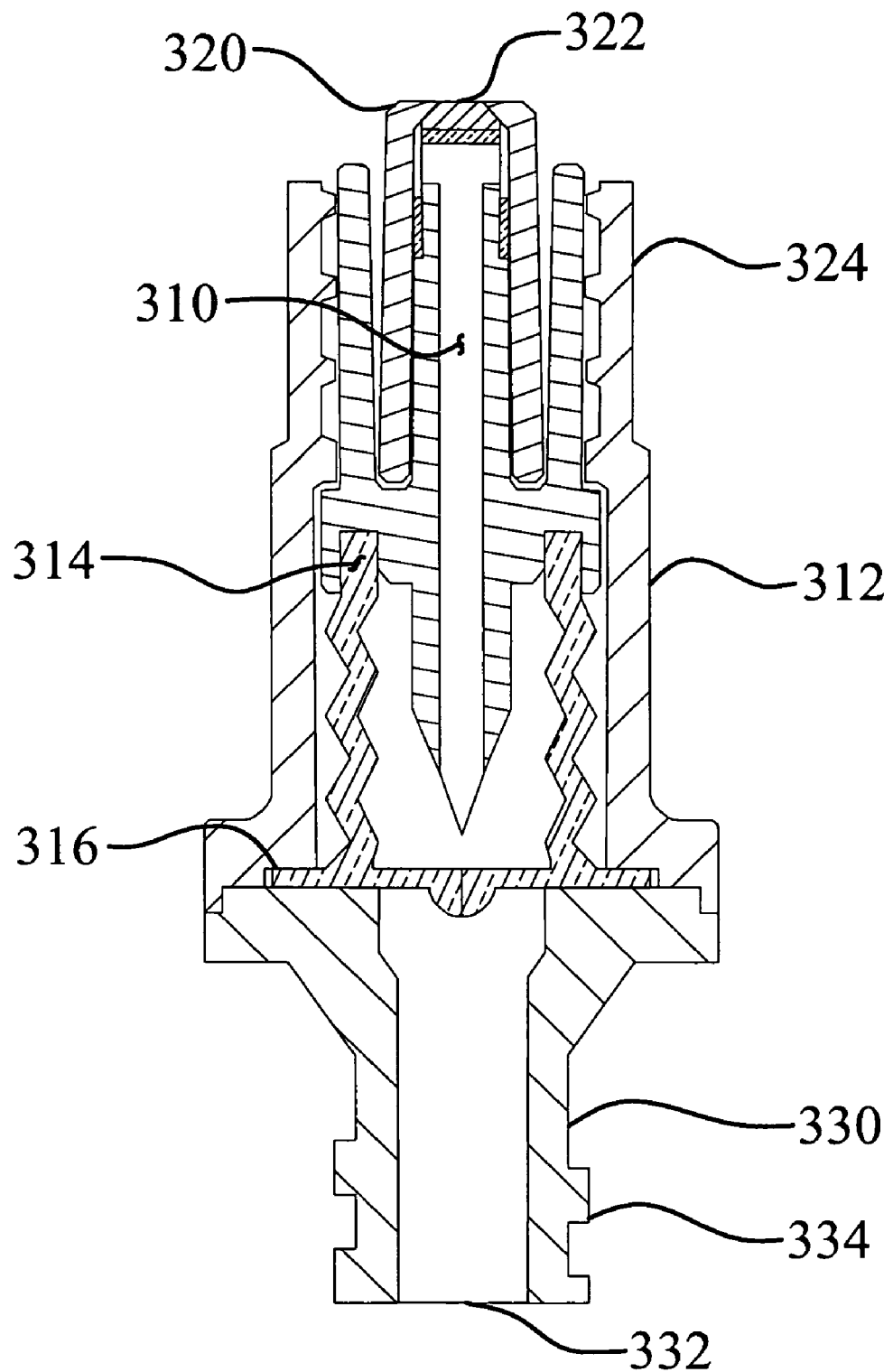
Figure 4:
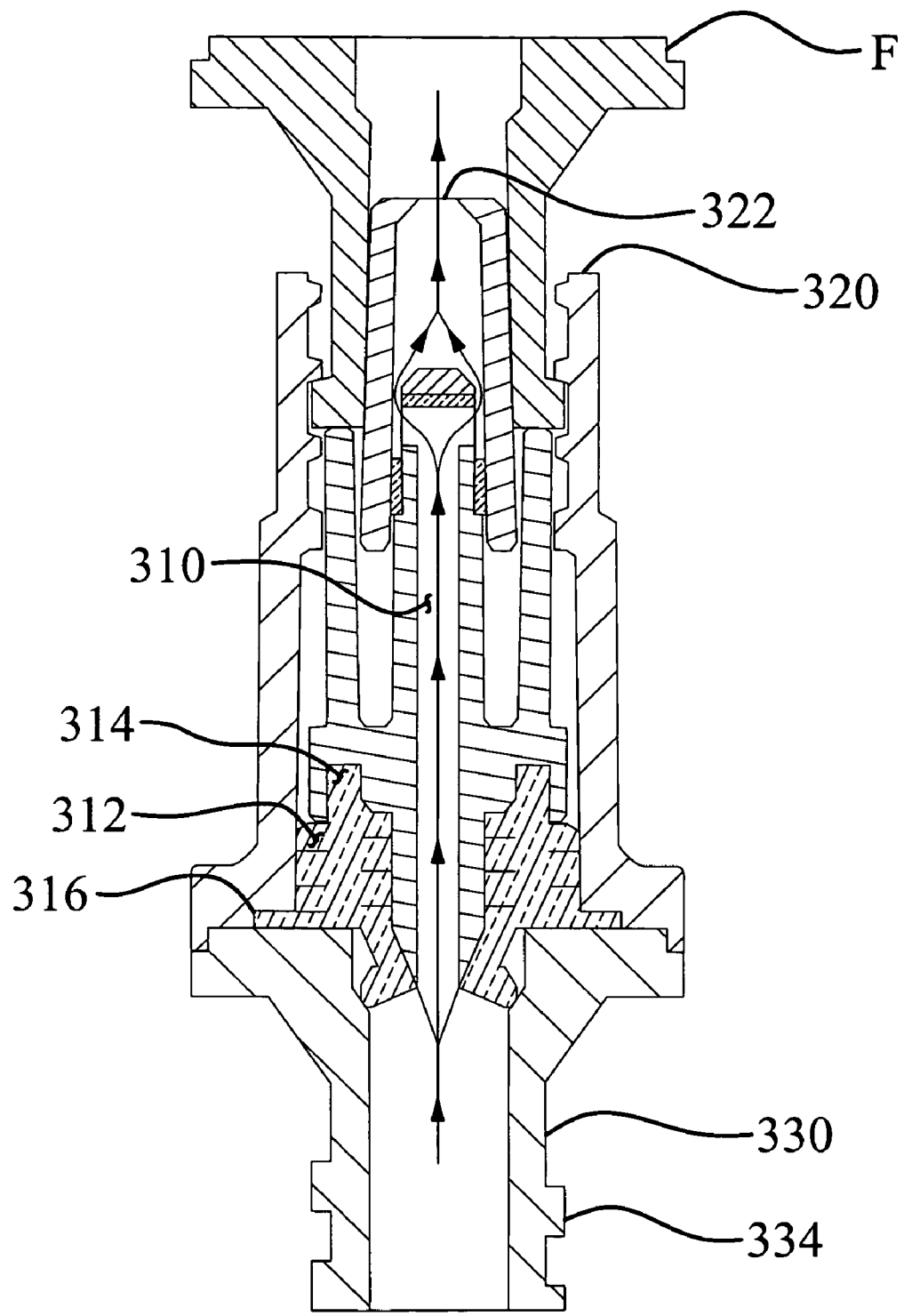

As seen in FIG. 1, the first piece of the apparatus (10) is a collection vessel (100) suitable for containing hazardous fluids, including by way of example and not limitation, radionuclides, chemotherapeutic agents, or other potentially toxic fluids. The collection vessel (100) is capable of containing a collection vessel volume (160), and has a collection vessel fluid port interlock (180), that is releasably attachable to a collection vessel connector (200). The collection vessel (100) also has a collection vessel internal channel (110) in fluid communication with the collection vessel volume (160) and in fluid communication with a collection vessel fluid port (170). The collection vessel fluid port is reversibly sealed from the environment by a collection vessel fluid port elastomeric closure (172) that is biased in favor of being sealed.

The second piece of apparatus, seen best in FIGS. 2a-2d, and in an alternative embodiment in FIGS. 3a-3d, is a collection vessel connector (200). By way of example, the embodiment seen in FIGS. 2a-2d may be better utilized when the collection vessel (100) is a bottle, and the embodiment seen in FIGS. 3a-3d may be better utilized when the collection vessel (100) is a bag. The collection vessel connector (200) has a collection vessel connector male end fluid port interlock (224) capable of releasably interlocking the collection vessel connector (200) to the collection vessel (100). In one embodiment, seen best in FIG. 2b and FIG. 8a, the collection vessel connector fluid male end fluid port interlock (224) is configured to snap around the connection vessel interlock (180) when the collection vessel (100) is in the shape of a bottle. In another embodiment, seen best in FIG. 3c, the collection vessel connector fluid male end fluid port interlock (224) is configured to grasp the collection vessel interlock (180) when the collection vessel (100) is in the shape of a bag, using a pincher-like motion. The collection vessel connector (200) also has a collection vessel connector male end fluid port (222) in fluid communication with a collection vessel connector internal channel (210). A connection vessel connector female end fluid port (232) is in fluid communication with the collection vessel connector internal channel (210). The collection vessel connector internal channel (210) contains a collection vessel connector deformable elastomeric valve (212) having a collection vessel connector deformable elastomeric valve male end (214) and a collection vessel connector deformable elastomeric valve female end (216). The collection vessel connector deformable elastomeric valve female end (216) reversibly seals the collection vessel female end fluid port (232) from the collection vessel internal channel (210), and the collection vessel connector elastomeric valve female end (216) is biased in favor of being sealed.

A collection vessel connector female end fluid port interlock (234) releasably attaches the collection vessel connector (200) to a first external device selected from the group of first external devices consisting of a dose control connector (300), a unit dose container (400), a delivery control connector (500), and a delivery site access device (600). While connection to all of these external devices is possible, in a preferred embodiment, the collection vessel female end fluid port interlock (234) releasably attached the collection vessel connector (200) to a dose control connector (300).

As seen best in FIGS. 4a-4e, the third piece of the apparatus (10) is the dose control connector (300) having a dose control connector male end fluid port interlock (324) capable of releasably interlocking the dose control connector (300) to a second external device selected from the group of second external devices consisting of the collection vessel connector (200), the delivery control connector (500), and the delivery site access device (600). While connection to all of these external devices is possible, in a preferred embodiment, the dose control connector male end fluid port interlock (324) releasably attaches the dose control connector (300) to the collection vessel connector (200) for filling the apparatus (10) with fluid, as described above; and to a delivery control connector (500) for discharging fluid from the apparatus, as will be detailed below.

The dose control connector (300) has a dose control connector male end fluid port (322) in fluid communication with a dose control connector internal channel (310). The dose control connector internal channel (310) contains a dose control connector deformable elastomeric valve (312) having a dose control connector deformable elastomeric valve male end (314) and a dose control connector deformable elastomeric valve female end (316). The dose control connector deformable elastomeric valve male end (312) reversibly seals the dose control male end fluid port (322) from the environment, and the dose control connector elastomeric valve male end (312) is biased in favor of being sealed. There is a dose control female end fluid port (332) in fluid communication with the dose control connector internal channel (310).

A dose control connector female end fluid port interlock (334) releasably attaches the dose control connector (300) to a third external device selected from the group of third external devices consisting of the unit dose container (400) and the delivery control connector (500). While connection to both of these external devices is possible, in a preferred embodiment, the dose control connector female end fluid port interlock (334) releasably attaches the dose control connector (300) to the unit dose container (400).

The fourth piece of the apparatus (10) is a unit dose container (400), best seen in FIGS. 5a-5b, which by way of example, may be a hypodermic syringe, containing a unit dose container volume (460). The unit dose container (400) has a unit dose container fluid port interlock (480) capable of releasably interlocking the unit dose container (400) to a fourth external device selected from the group of fourth external devices consisting of the collection vessel connector (200), the dose control connector (300), the delivery control connector (500), and the delivery site access device (600). While connection to all of these external devices is possible, in a preferred embodiment, the unit dose container fluid port interlock (480) releasably attaches the unit dose container (400) to the dose control connector (300).

The unit dose container (400) has a unit dose container internal channel (410) in fluid communication with the unit dose container volume (460) and in fluid communication with a unit dose container fluid port (470). There is a unit dose container fluid manipulation regulator (490) regulating the unit dose container volume (460), which may, by way of example and not limitation, be a syringe barrel piston.

The fifth piece of the apparatus (10) is the delivery control connector (500), best seen in FIGS. 6a-6e, having a delivery control connector male end fluid port interlock (524) (see FIG. 13c) capable of releasably interlocking the delivery control connector (500) to a fifth external device selected from the group consisting of the collection vessel connector (200), the dose control connector (300), and the delivery site access device (600). While connection to all of these external devices is possible, in a preferred embodiment, the delivery control connector male end fluid port interlock (524) releasably attaches the delivery control connector (500) to the delivery site access device (600).

The delivery control connector (500) has a delivery control connector male end fluid port (522) in fluid communication with a delivery control connector internal channel (510). The delivery control connector internal channel (510) contains a delivery control connector deformable elastomeric valve (512) having a delivery control connector deformable elastomeric valve male end (514) and a delivery control connector deformable elastomeric valve female end (516).

There is a delivery control female end fluid port (532) in fluid communication with the delivery control connector internal channel (510). The delivery control deformable elastomeric valve female end (516) reversibly seals the delivery control female end fluid port (532) from the environment, and the delivery control connector elastomeric valve female end (516) is biased in favor of being sealed.

There is a delivery control connector female end fluid port interlock (334e) capable of releasably interlocking the delivery control connector (500) to a sixth external device selected from the group consisting of the unit dose container (400) and the dose control connector (300). While connection to both of these external devices is possible, in a preferred embodiment, the delivery control connector female end fluid port interlock (234) releasably attaches the delivery control connector (500) to a dose control connector (300).

Figure 7:
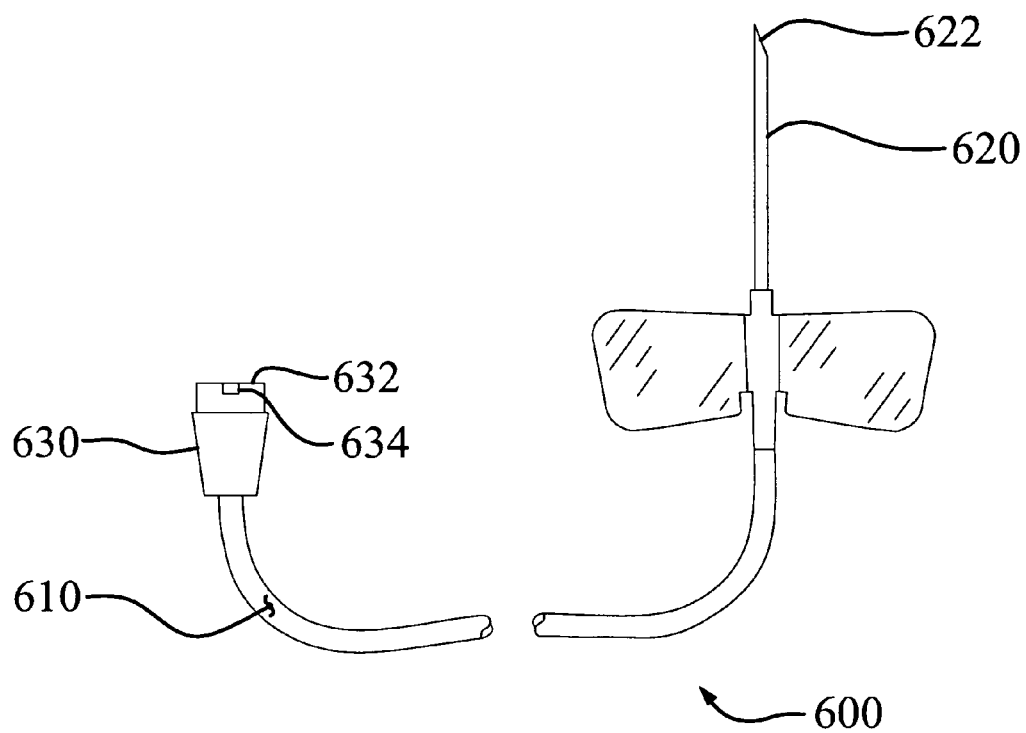
FIG. 7 is a side elevation view of an embodiment of a delivery site access device (600) of the instant invention, not to scale.
Figure 8:
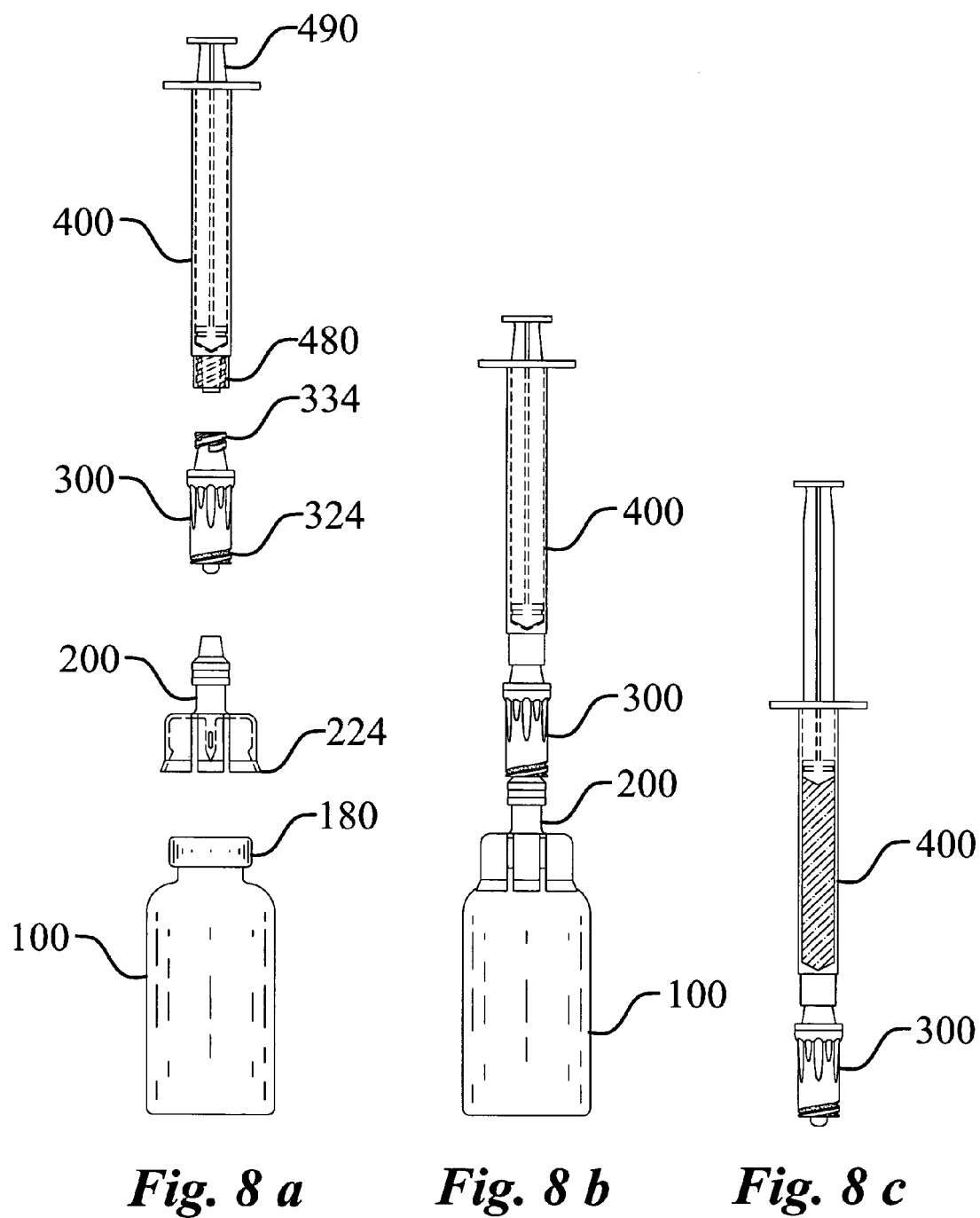
FIG. 8a is an exploded view of the apparatus (10) illustrating an embodiment of an assembly of a collection vessel (100), a collection vessel connector (200), a dose control connector (300) and a unit dose container (400), of the instant invention, not to scale.
FIG. 8b is a view of the elements seen in FIG. 8a in their assembled state, ready for the dispensing of a hazardous fluid from the collection vessel (100) to the unit dose container (400), not to scale.
FIG. 8c is a view of the assembled dose control connector (300) and fluid filled unit dose container (400), ready for transport to an intended place of use, not to scale.

The sixth piece of the apparatus (10) is the delivery site access device (600), best seen in FIG. 7, having a delivery site access device delivery site end (620) in fluid communication with a delivery site access device delivery site end fluid port (622). There is a delivery site access device female end (630) having a delivery site access device fluid port (632) in fluid communication with a delivery site access device internal channel (610) and thence to a delivery site (S). By way of example, this may be a plastic catheter inserted in a vein or other intended delivery site, or may be any of a number of delivery site access devices using a metal needle to access an intended delivery site, as seen in best in FIG. 7 and FIGS. 9-11.

The delivery site access device (600) has a delivery site female end fluid port interlock (634), also seen in FIG. 7, capable of releasably interlocking the delivery site access device (600) to a seventh external device selected from the group consisting of the unit dose container (400), the dose control connector (300), and the delivery control connector (500). While connection to all of these external devices is possible, in a preferred embodiment, the delivery site female end fluid port interlock (634), releasably attaches the delivery site access device (600) to a delivery control connector (500).

While it is entirely feasible for a single person, or persons in a single location, to assemble all of the apparatus (10) enumerated above, in a preferred embodiment the first, second, third and fourth pieces may be assembled in a first site such as a pharmacy or other preparation area, while the fifth and sixth pieces may be assembled by another person, or persons, at a second site, such as an intended point of use.

The apparatus (10) may exist in any number of alternative embodiments. In one embodiment, by way of example only, and not limitation, the dose control connector internal channel deformable elastomeric valve female end (316) reversibly seals the dose control female end fluid port (332) from the environment, the dose control connector elastomeric valve female end (316) being biased in favor of being sealed.

In another embodiment, again by way of example only, and not limitation, the delivery control connector deformable elastomeric valve male end (514) reversibly seals the delivery control male end fluid port (522) from the environment, and the delivery control connector elastomeric valve male end (514) is biased in favor of being sealed.

In yet another embodiment, the collection vessel fluid port elastomeric closure (172) may further comprise a collection vessel fluid port puncturable resealable elastomeric seal (174), seen best in FIG. 1c. The collection vessel connector male end fluid port (222) may further comprise a collection vessel connector male end fluid port ingress means (223) capable of reversibly traversing the collection vessel fluid port puncturable resealable elastomeric seal (174), and thus placing the collection vessel connector male end fluid port (222) in fluid communication with the collection vessel volume (160). A typical example of such an embodiment may be as best seen in FIGS. 2b and 3c.

In one embodiment, seen in FIG. 2b, the collection vessel internal channel deformable elastomeric valve male end (214) lacks a sealing capacity, thus, when the collection vessel male end fluid port (222) is placed in fluid communication with the collection vessel volume (160), the collection vessel connector internal channel (210) is placed in fluid communication with the collection vessel volume (160), and depends on the collection vessel connector deformable internal channel elastomeric valve female end (216) to isolate the collection volume (160) from the environment. In yet another embodiment, the collection vessel internal channel deformable elastomeric valve male end (214) may be capable of sealing the collection vessel connector male end fluid port (222) from the environment, and the collection vessel internal channel deformable elastomeric valve male end (214) is biased in favor of being sealed.

As seen in FIGS. 6d-6e, a particular type of elastomeric valve closure seen in the prior art, such as that taught by Leinsing in U.S. Pat. No. 6,142,446; may be useful as part of an embodiment of the apparatus (10). These types of closures use a generally barrel shaped elastomeric component contained within the lumen of a connector, at the female end of the connector, shown in FIGS. 6d-6e as a dose control connector (300) but which is equally applicable in the construction of a collection vessel connector (200), and a delivery control connector (500). For the purposes only of illustrating this embodiment, the female end of the dose control connector (300) is the only end shown in FIGS. 6d-6e.

As seen in FIG. 4e, an effect of the disconnection of the valve (312) and the concomitant increase of the internal volume of the valve (312) is that a decreased pressure is created at the fluid port (332) as the valve (312) is closing. This creates a tendency for a fluid on the surface of the fluid port (332) to be drawn back into the internal channel (310), rather than being left on the surface of the fluid port (332). Thus, in such an embodiment, the instant invention not only increases safety by eliminating needles or other sharp objects from the apparatus (10), but increases safety by having substantially all of the fluid left on the female end of the fluid ports (e.g., 232, 332, 532, and 632) drawn back into the related connectors (200, 300, 500, and 600) rather than being left behind to contaminate the environment.

In a common embodiment, the potentially interlocking mating pairs of connectors enumerated above, may be formed using standard sized and designed connectors such as would be known to one skilled in the art, and as are commonly called "Luer lock" connectors. Such an embodiment has the advantage of making the apparatus (10) detailed above compatible with standard syringes and intravenous tubing. However, as a safety and security measure, it may be desirable to configure the potentially interlocking pairs of connectors using a unique interlock safety feature. As would be known to one skilled in the art, such interlock safety features could encompass color coding, non-standard interlock shape or sizing, reverse threads on the interlocks, or a unique mating key system. This would present a unique safety check such that potentially dangerous materials could only be administered using a complete and compatible apparatus (10).

A possible scenario utilizing such an embodiment is easy to construct. An interlock safety featured system might be used, by way of example only, for the administration of radioactive radionuclide imaging agents in a medical diagnostic setting, such as a hospital or other diagnostic facility. Specially trained and equipped nuclear medicine pharmacy workers could prepare a radionuclide agent in a suitable collection vessel (100) having a collection vessel interlock (180) that was equipped with a particular first interlock safety feature (555). This collection vessel could then only be accessed by a uniquely mated collection vessel connector (200) having a corresponding second interlock safety feature (666) and the radionuclide could only be drawn into dose control connectors (300) and unit dose containers (400) that have compatibly configured interlock safety features. The resulting apparatus (10) may then be transported in a suitable container to an intended site of use. Meanwhile, a patient caregiver could insert a delivery site access device (600) having compatibly configured interlock safety features into an intended access site such as the vein of a patient. A delivery control connector (500), again having a compatibly configured interlock safety feature could then be attached to the delivery site access device (600) to await administration of the radionuclide. It would be possible for each pair of possible mating components to have a interlock safety feature unique to appropriate pairings, by way of example only, such as the collection female end fluid port interlock (234) and the dose control connector male end fluid port interlock (324); or dose control connector male end fluid port interlock (324) to the delivery control connector female end fluid port interlock (534). However, since one object of the interlock safety feature system is to prevent the apparatus (10) from being compatible with standard fluid handling equipment, it would be possible, and one skilled in the art could choose, to have one type of interlock, a first interlock safety feature (555) as part of the collection vessel fluid port interlock (180) and a second interlock safety feature (666) as part of the collection vessel male end fluid port interlock (224).

In another embodiment, the collection vessel connector female end fluid port interlock (234), the dose control connector female end fluid port interlock (334), delivery control connector female end fluid port interlock (534), and the delivery site access device female end fluid port interlock (634) all further comprise a third interlock safety feature (777), that is capable only of mating with a fourth interlock safety feature (888), found on the dose control connector male end fluid port interlock (324), the delivery control connector male end fluid port interlock (524), and the unit dose container fluid port interlock (480), as seen in FIGS. 12b-12c.

By way of example only, and not limitation, a particular configuration of interlock safety features could be employed by a nuclear medicine department, that, by restricting access to the unique components of the apparatus, would help insure that only specially trained and authorized personnel would have access to the apparatus, and thus would decrease the chances of unauthorized administration. Also by way of example only, a facility could use different particular interlock safety features in different areas, such as having different safety features in apparatus (10) intended for the nuclear medicine and, by way of another example, for a chemotherapeutic team; again to insure only authorized administration.

If lesser security is desired, standard size or shape interlocks may be used, but the apparatus (10) may be configured to still be visually compatible, such as by making the collection vessel (100), the collection vessel connector (200), the dose control connector (300), the unit dose container (400), the delivery control connector (500), and the delivery site access device (600), matched in coloration when intended for a particular use. For speed of connection, it may be desirable to use a simple luer slip in place of the luer lock.

Such embodiments would necessarily present several advantages. Any person handling the apparatus (10) would be aware, by virtue of its non-standard interlock safety features, that this is a special apparatus (10) requiring special handling. It would be very difficult to inject a substance contained in the apparatus (10) to a patient with a standard delivery site access device, such as routinely found in intravenous tubing. Thus, by controlling caregiver access to certain portions of the apparatus (10) to the specially trained, safety and accountability are increased.

The apparatus (10) may also be configured in such a manner that one or more of the pieces of apparatus (10) are permanently, rather than releasably, attached to one another. This has the advantage of decreasing the total number of parts, decreasing the complexity of certain of the parts, and increasing the likelihood that pieces of the apparatus (10) will not be interchangeable with standard fluid handling devices. While a detailed description of such an apparatus (10) using certain permanently attached pieces follows immediately below; in essence, the apparatus (10) differs in such an embodiment form that above in that the dose control connector (300) and the unit dose container (400) are permanently attached to one another, and may in fact be integrally formed; and the delivery site access device (600) and the delivery control connector (500) are permanently attached to one another, and may in fact be integrally formed.

In detail, in a typical embodiment using fused pieces of apparatus, a collection vessel (100) containing a collection vessel volume (160) further comprises a collection vessel fluid port interlock (180), releasably attachable to a collection vessel connector (200). A collection vessel internal channel (110) is in fluid communication with the collection vessel volume (160) and in fluid communication with a collection vessel fluid port (170) reversibly sealed from the environment by a collection vessel fluid port elastomeric closure (172) that is biased in favor of being sealed, as seen in other embodiments seen in FIGS. 1a-3d.

The collection vessel connector (200) has a collection vessel male end (220) and a collection vessel female end (230) and further comprising a collection vessel connector male end fluid port interlock (224) releasably interlocking the collection vessel connector (200) to the collection vessel (100). A collection vessel connector male end fluid port (222) is in fluid communication with a collection vessel connector internal channel (210) and a connection vessel connector female end fluid port (232) is in fluid communication with the collection vessel connector internal channel (210).

The collection vessel connector internal channel (210) contains a collection vessel connector deformable elastomeric valve (212) having a collection vessel connector deformable elastomeric valve male end (214) and a collection vessel connector deformable elastomeric valve female end (216). The collection vessel connector deformable elastomeric valve female end (216) reversibly seals the collection vessel female end fluid port (232) from the collection vessel internal channel (210), and the collection vessel connector elastomeric valve female end (216) is biased in favor of being sealed.

A collection vessel connector female end fluid port interlock (234) releasably attaches the collection vessel connector (200) to a dose control connector (300); and the dose control connector (300) has a dose control connector male end (320) and a dose control connector female end (330). A dose control connector male end fluid port interlock (324) releasably attaches the dose control connector (300) to an eighth external device selected from the group of eighth external devices consisting of the collection vessel connector (200) and the livery control connector (500). While connection to both of these external devices is possible, in a preferred embodiment, the dose control connector male end fluid port interlock (324), releasably attaches the dose control connector (300) to a collection vessel connector (200) when filling the apparatus (10) with fluid, or to a delivery control connector (500) when discharging fluid from the apparatus, both of which have been previously described.

Figure 10:
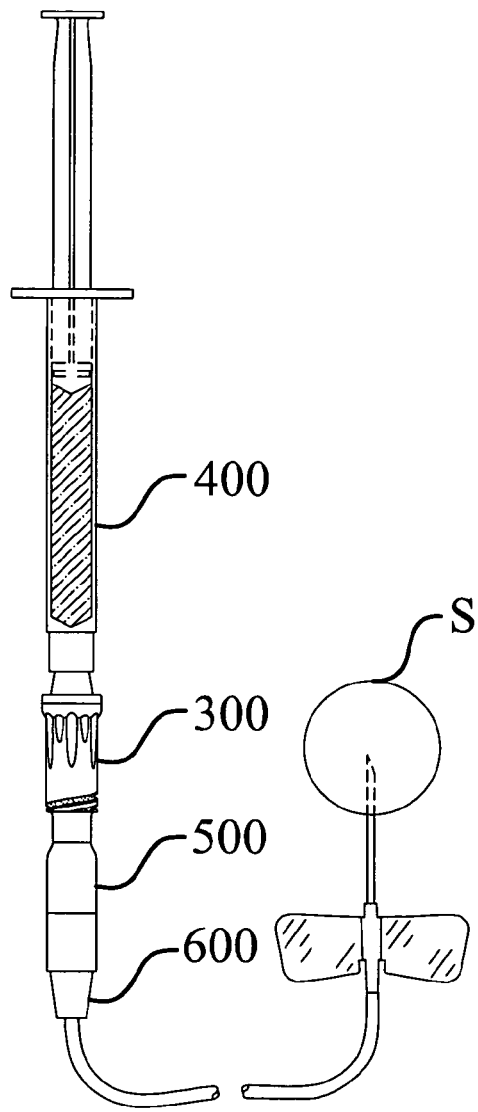
FIG. 10 is a view of the assemblage of a delivery site access device (600), a delivery control connector (500), a dose control connector (300), and a unit dose container (400); ready for the dispensing of a hazardous fluid from the unit dose container (400) to a schematically represented delivery site (S), not to scale.
Figure 11:
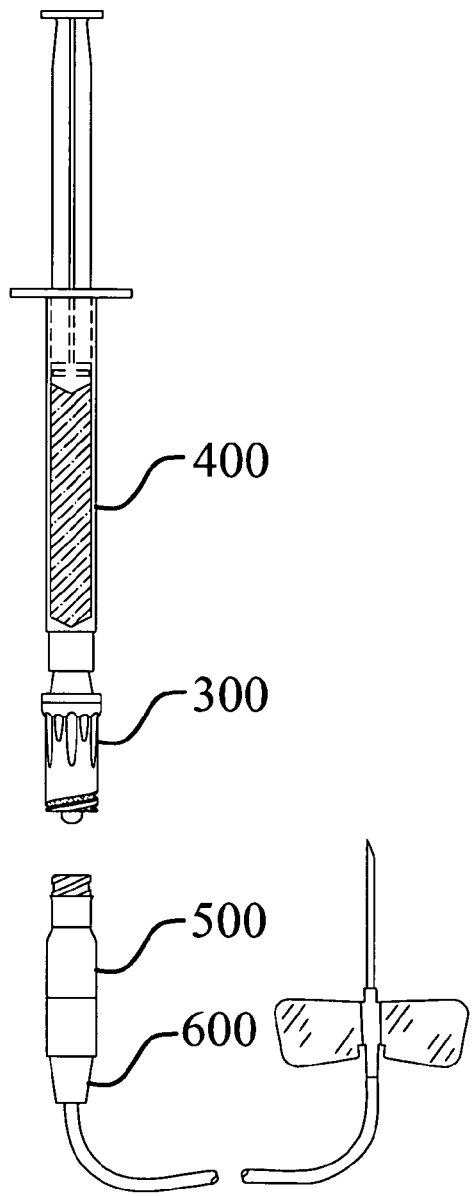
FIG. 11 is a view of an interlocked dose control connector (300) and unit dose container (400); detached from an interlocked delivery site connector (500) and delivery site access device (600); after the dispensing of a hazardous fluid from the unit dose container (400) to a schematically represented delivery site (S), ready for transport for disposal, not to scale.
Figure 12:
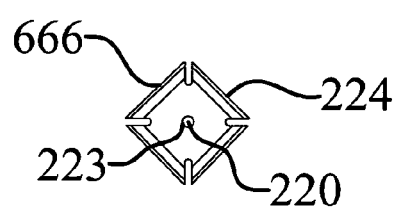
FIG. 12a is a top plan view of an alternate embodiment of a collection vessel connector male end fluid port interlock (224), showing a second interlock safety feature (666) in the shape of a square, by means of example only, of a non-standard shaped interlock, not to scale.
FIG. 12b is a top plan view of an alternate embodiment of a collection vessel fluid port interlock (180), showing a first interlock safety feature (555) in the shape, by means of example only, of a square shaped interlock, not to scale.
FIG. 12c is an exploded view of an embodiment of an assemblage of a collection vessel (100), a collection vessel connector (200), a unit dose connector (300), and a unit dose container (400); showing third (777) and fourth (888) interlock safety features in the form, by means of example only, of reverse (left-hand) threads, not to scale.
Figure 12:
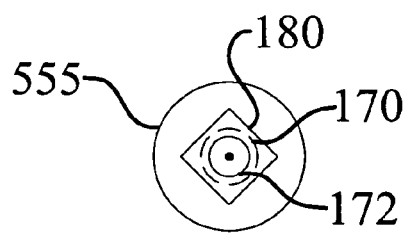
Figure 12:
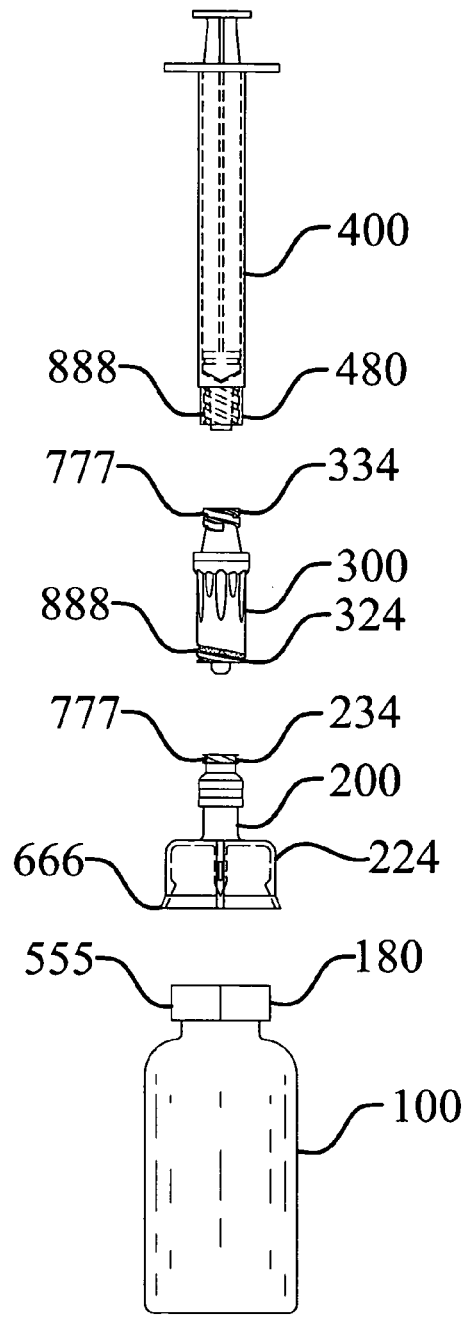
Figure 13:
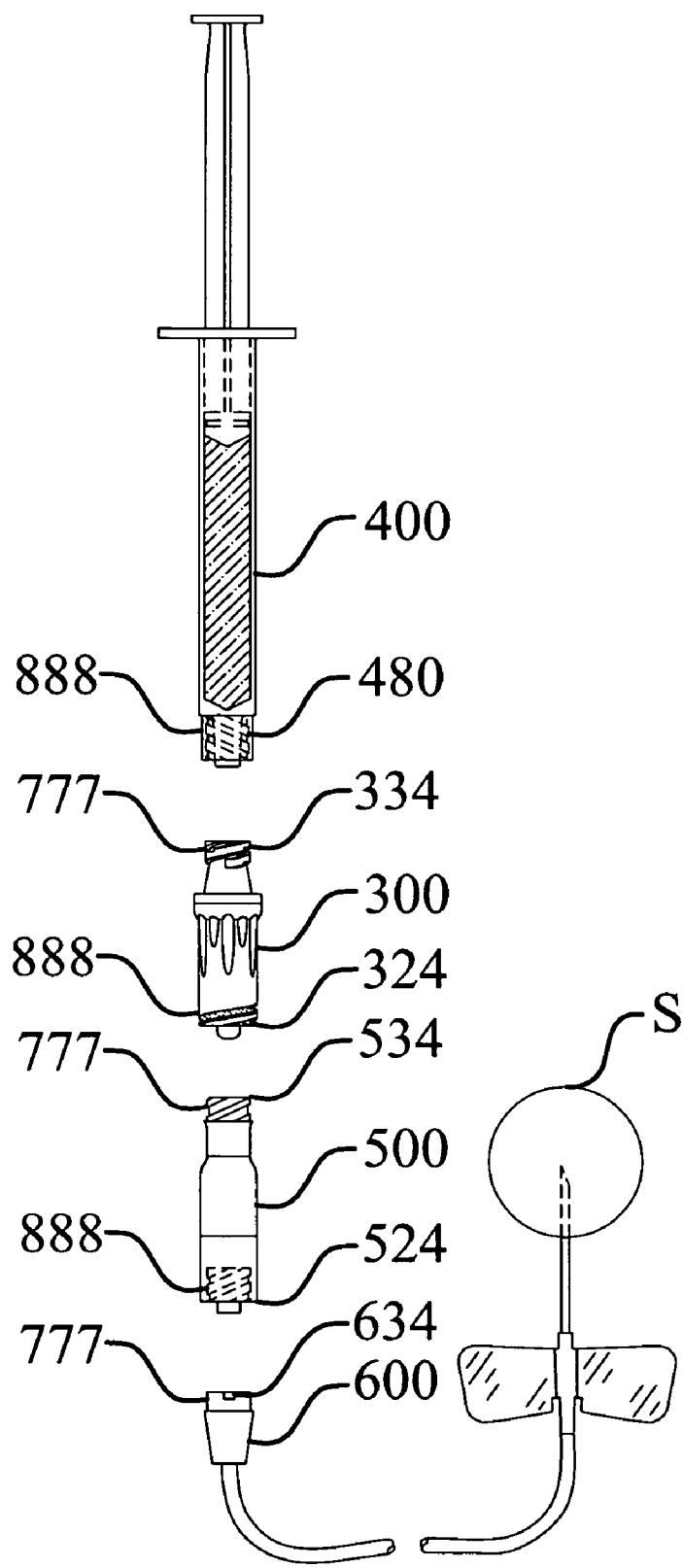
FIG. 13a is a side elevation view of an embodiment of a unit dose container (400) and a dose control connector (300) in which the unit dose container (400) and a dose control connector (300) are permanently joined as a single unit, not to scale.
FIG. 13b is a side elevation view of an embodiment of a delivery site access device (600) and a delivery control connector (500) in which the delivery site access device (600) and a delivery control connector (500) are permanently joined as a single unit, not to scale.
FIG. 13c is an exploded view of an assemblage of a unit dose container (400), a dose control connector (300), a delivery control connector (500), and a delivery site access device (600) showing the connection to a to a schematically represented delivery site (S), in which third interlock safety features (777) cooperate with mating fourth interlock safety features (888), not to scale.

It will be appreciated by one skilled in the art that embodiments wherein the dose control connector (300) is permanently attached to the unit dose container (400), or wherein the delivery control connector (500) is permanently attached to the delivery site access device (600), may not look appreciably different on the outside from embodiments utilizing individually separable components, for example, the components seen assembled in FIGS. 10 and 11. However, one skilled in the art will also realize that permanent connection among various components may result in a somewhat different, and reduced complexity, structure.

As seen in FIG. 13a, a dose control connector male end fluid port (322) is in fluid communication with a dose control connector internal channel (310); and the dose control connector internal channel (310) contains a dose control connector deformable elastomeric valve (312) having a dose control connector deformable elastomeric valve male end (314) and a dose control connector deformable elastomeric valve female end (316).

The dose control connector deformable elastomeric valve male end (312) reversibly seals the dose control male end fluid port (322) from the environment, and the dose control connector elastomeric valve male end (312) is biased in favor of being sealed. A dose control female end fluid port (332) is in fluid communication with the dose control connector internal channel (310). A dose control connector female end fluid port interlock (334) permanently attaches the dose control connector (300) to the unit dose container fluid port interlock (480), again as externally appears as in FIG. 13a.

The unit dose container (400) contains a unit dose container volume (460), and further comprises a unit dose container fluid port interlock (480) permanently interlocking the unit dose container (400) to the dose control connector (300). A unit dose container internal channel (410) is in fluid communication with the unit dose container volume (460) and in fluid communication with a unit dose container fluid port (470).

A unit dose container fluid manipulation regulator (490) regulates the unit dose container volume (460); and the unit dose container fluid port interlock (480) permanently attaches the unit dose container (400) to the dose control connector female end fluid port interlock (334). The delivery control connector (500) has a delivery control connector male end (520) and a delivery control connector female end (530) and further comprises a delivery control connector male end fluid port interlock (524) permanently interlocking the delivery control connector (500) to a delivery site access device female end fluid port interlock (634).

As seen in FIG. 13b, a delivery control connector male end fluid port (522) is in fluid communication with a delivery control connector internal channel (510); and the delivery control connector internal channel (510) contains a delivery control connector deformable elastomeric valve (512) having a delivery control connector deformable elastomeric valve male end (514) and a delivery control connector deformable elastomeric valve female end (516). A delivery control female end fluid port (532) is in fluid communication with the delivery control connector internal channel (510).

The delivery control deformable elastomeric valve female end (516) reversibly seals the delivery control female end fluid port (532) from the environment, and the delivery control connector elastomeric valve female end (516) is biased in favor of being sealed. A delivery control connector female end fluid port interlock (534) releasably attaches the delivery control connector (500) the dose control connector (300).

The delivery site access device (600) has a delivery site access device delivery site end (620) and a delivery site access device female end (630) and further comprises a delivery site access device delivery site end (620) having a delivery site access device delivery site end fluid port (622) in fluid communication with a delivery site access device internal channel (610). A delivery site access device female end (630) has a delivery site access device female end fluid port (632) in fluid communication with the delivery site connector internal channel (610), again as would externally appear as in FIG. 13*b*.

A delivery site access device female end fluid port interlock (634) permanently attaches the delivery site access device (600) to the delivery control connector male end fluid port interlock (524).

The instant invention also includes embodiments for methods for the handling of a hazardous fluid. Such a method may be described as being performed both by a "preparer" and an "administrator," although one skilled in the art will realize that such roles as exemplary only and may, in fact, be accomplished by one person.

Such a method includes a preparer first enclosing a collection vessel volume (160) to be handled in a collection vessel (100) further comprising a collection vessel fluid port interlock (180), releasably interlockable to a collection vessel connector male end fluid port interlock (224). There is a collection vessel internal channel (110) in fluid communication with the collection vessel volume (160) and in fluid communication with a collection vessel fluid port (170) being reversibly sealed from the environment by a collection vessel fluid port elastomeric closure (172) being biased in favor of being sealed.

Next, as illustrated in FIG. 8*a* and in FIGS. 2*a*-3*d*, the preparer releasably interlocks the collection vessel connector male end fluid port interlock (224) to the collection vessel fluid port interlock (180), thereby interlocking to the collection vessel (100) a collection vessel connector (200) having a connector vessel connector male end (220) and a collection vessel connector female end (230). The connector vessel connector (200) further comprises the collection vessel connector male end fluid port interlock (224); a collection vessel connector male end fluid port (222) in fluid communication with a collection vessel connector internal channel (210), and a connection vessel connector female end fluid port (232) in fluid communication with the collection vessel connector internal channel (210). The collection vessel connector internal channel (210) contains a collection vessel connector internal channel deformable elastomeric valve (212) having a collection vessel connector internal channel deformable elastomeric valve male end (214) and a collection vessel connector internal channel deformable elastomeric valve female end (216).

The collection vessel connector internal channel deformable elastomeric valve female end (216), seen best in FIGS. 2*a*-2*d*, reversibly seals the collection vessel connector female end fluid port (232) from the collection vessel internal channel (210), and the collection vessel connector internal channel deformable elastomeric valve female end (216) is biased in favor of being sealed. There is additionally a collection vessel connector female end fluid port interlock (234).

The interlocking of the collection vessel connector (200) to the collection vessel (100), seen best in FIGS. 8*a*-8*b*, causes the collection vessel fluid port elastomeric closure (172), seen in FIG. 1*b*, to reverse bias and become opened, thereby placing the collection vessel volume (160) in fluid communication with the collection vessel connector male end fluid port (222) and thereby in fluid communication with the collection vessel connector internal channel (210).

As illustrated in FIG. 8*a* and FIG. 5*a*, the preparer then releasably interlocks a unit dose container male end fluid port interlock (480) to a dose control connector fluid port interlock (334), thereby interlocking a unit dose container (400) to a dose control connector (300) further comprising the unit dose container fluid port interlock (480) and a unit dose container internal channel (410) in fluid communication with a unit dose container volume (460) and in fluid communication with a unit dose container fluid port (470). There is a unit dose container fluid manipulation regulator (490) regulating the unit dose container volume (460).

As illustrated in FIGS. 8*a*-8*b*, the preparer then releasably interlocks a dose control connector male end fluid port interlock (324) to the collection vessel connector female end fluid port interlock (234), thereby interlocking to the collection vessel connector (200) the dose control connector (300) having a dose control connector male end (320) and a dose control connector female end (330). The dose control connector (300) further comprises the dose control connector male end fluid port interlock (324) and a dose control connector male end fluid port (322) in fluid communication with a dose control connector internal channel (310). The dose control connector internal channel (310) contains a dose control connector deformable elastomeric valve (312) having a dose control connector deformable elastomeric valve male end (314) and a dose control connector deformable elastomeric valve female end (316). The dose control connector deformable elastomeric valve male end (312) reversibly seals the dose control connector male end fluid port (322) from the environment, and the dose control connector elastomeric valve male end (312) is biased in favor of being sealed.

As seen in FIGS. 4*a*-4*e*, there is a dose control connector female end fluid port (332) in fluid communication with the dose control connector internal channel (310), and with the unit dose container male fluid port (470).

Next, the interlocking of the dose control connector (300) to the collection vessel connector (200) causes the collection vessel connector deformable elastomeric valve female end (216), seen in FIGS. 2*b* and 3*d*, and the dose control connector deformable elastomeric valve male end (314) to reverse bias and become opened, thereby placing the collection vessel volume (160) in fluid communication with the dose control connector male end fluid port (322) and thereby in fluid communication with the dose control connector internal channel (310).

The interlocking of the unit dose container (400) to the dose control connector (300) places the unit dose container volume (460) in fluid communication with the unit dose connector internal channel (310), thence with the collection vessel connector internal channel (210) and thence with the collection vessel volume (160). The apparatus (10) is seen in exploded view in FIG. 8*a*, and in the assembled, ready to dispense configuration, in FIG. 8*b*.

The preparer then withdraws a predetermined amount of a hazardous fluid from the collection vessel (100) through the collection vessel connector (200) thence through the dose control connector (300) and thence into the unit dose container (400) by manipulation of the unit dose container fluid manipulation regulator (490), as may be seen from FIG. 8b.

The preparer next releasably detaches the dose control connector (300) from the collection vessel connector (200), the act of disengaging including the disengaging of the collection vessel connector female end fluid port interlock (234) and the dose control connector male end fluid port interlock (324), said disengaging causing the dose control connector internal channel deformable elastomeric valve male end (314) and the collection vessel connector internal channel deformable elastomeric valve female end (216) to reverse bias and become sealed, thereby reversibly interrupting the fluid communication between the dose control connector internal channel (310) and the collection vessel connector internal channel (210). The unit dose container (400) and the dose control connector may be seen, ready for transport and administration, in FIG. 8c.

The preparer or some other person then suitably transports the connected dose control connector (300) and unit dose container (400) to a point of use; whereupon the method will be employed by a person, called, by way of example only, the "administrator."

Figure 9:
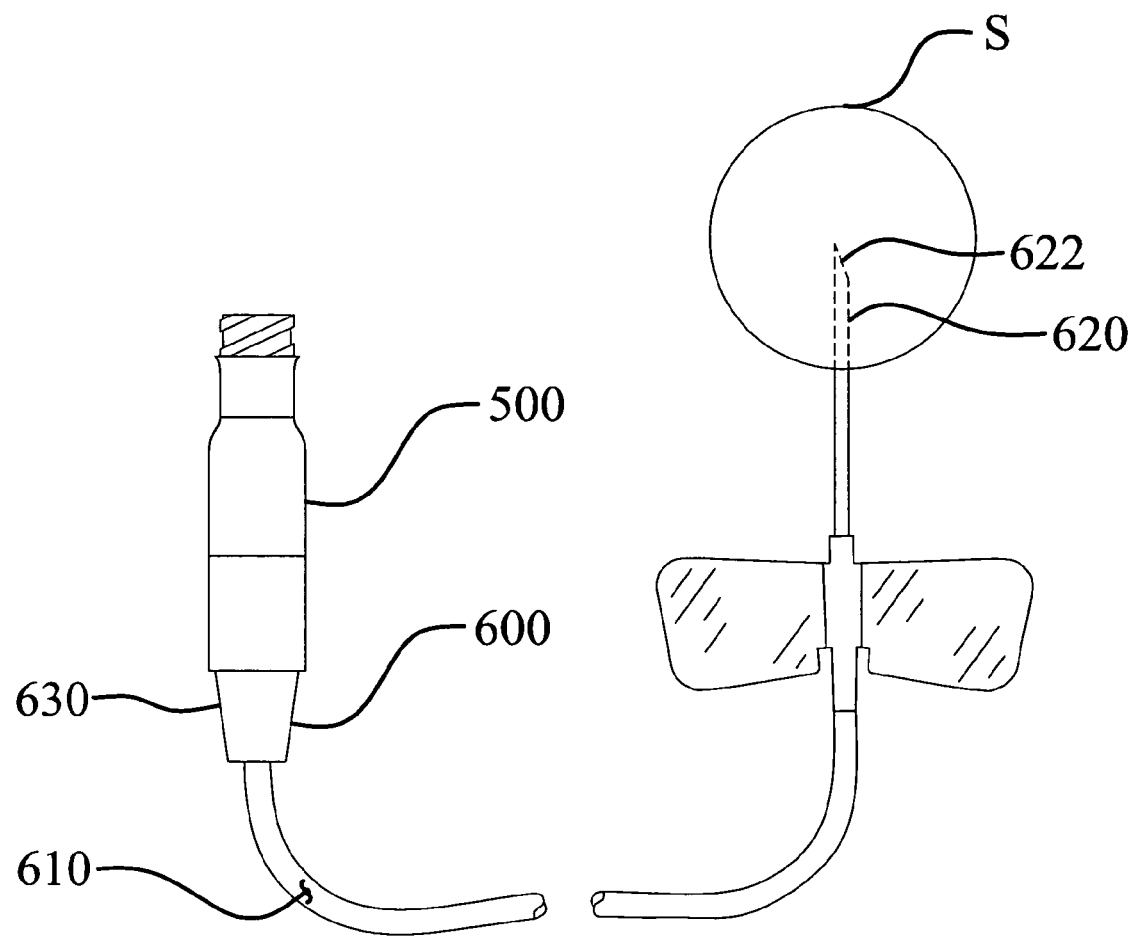
FIG. 9 is a view of the assemblage of a delivery control connector (500) and a delivery site access device (600), showing the delivery site access device (600) accessing a schematically represented delivery site (S), not to scale.

The administrator, as illustrated in FIG. 9, first releasably attaches a delivery site access device (600) having a delivery site access device delivery site end (620) and a delivery site access device delivery site end fluid port (622) to a delivery site (S), thereby attaching to the delivery site (S) a delivery site access device (600) having a delivery site access device female end (630). By way of example, and not limitation, a delivery site may be the lumen of a blood vessel.

The delivery site access device (600) further comprises a delivery site access device female end fluid port interlock (634); and a delivery site access device female end fluid port (632) in fluid communication with a delivery site access device internal channel (610), thence to the delivery site end fluid port (622), and thence to the delivery site (S), as seen in FIG. 7 and FIGS. 9-11.

The administrator then releasably interlocks a delivery control connector male end fluid port interlock (524) to the delivery site access device female end fluid port interlock (634), as seen in FIGS. 6a-6d, FIG. 9 and FIG. 13c, thereby attaching to the delivery site (S) a delivery control connector (500) having a delivery control connector male end (520) and a delivery control connector female end (530) further comprising; the delivery control connector male end fluid port interlock (524); and a delivery control connector male end fluid port (522) in fluid communication with a delivery control connector internal channel (510). The delivery control connector internal channel (510) contains a delivery control connector internal channel deformable elastomeric valve (512) having a delivery control connector internal channel deformable elastomeric valve male end (514) and a delivery control connector internal channel deformable elastomeric valve female end (516).

As seen in FIGS. 6a-6d, there is a delivery control connector female end fluid port (532) in fluid communication with the delivery control connector internal channel (510); wherein the delivery control connector internal channel deformable elastomeric valve female end (516) reversibly seals the delivery control connector female end fluid port (532) from the environment, and the delivery control connector internal channel elastomeric valve female end (516) is biased in favor of being sealed.

The interlocking of the delivery control connector (500) to the delivery site access device (600) places the delivery site in fluid communication with the delivery site access device internal channel (610), seen in FIG. 9.

The administrator next releasably interlocks the dose control connector male end fluid port interlock (324) and the delivery control connector female end fluid port interlock (534), thereby interlocking the dose control connector (300) and the delivery control connector (500); said interlocking causing the dose control connector internal channel deformable elastomeric valve male end (314) and the delivery control connector internal channel deformable elastomeric valve female end (516) to reverse bias and become opened, and thereby to place the delivery control connector internal channel (510) and the dose control connector internal channel (310) in open fluid communication with the unit dose container volume (460). The interlocked unit dose container (400) and dose control connector (300), and the interlocked delivery site connector (500) and the delivery site access device (600) are shown ready for interlocking in FIG. 11, and interlocked and ready to dose in FIG. 10.

The administrator may then dispense the hazardous fluid from the unit dose container (400) through the dose control connector (300) thence through the delivery control connector (500) and thence through the delivery site access device (600) to the delivery site (S) by means of manipulating the unit dose container fluid manipulation regulator.

Next, the administrator releasably detaches the dose control connector (300) from the delivery control connector (500), the act of disengaging including the disengaging of the dose control connector male end fluid port interlock (324) and the delivery control connector female end fluid port interlock (534) interlock, said disengaging causing the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510). The connected unit dose container (400) and the dose control connector (300); and the connected delivery site connector (500) and delivery site access device (600) are shown disassembled in FIG. 11.

In suitable embodiments using appropriate connectors (200, 300, 500, and 600), detailed above, the method may be practiced such that the step of disengaging the dose control connector (300) and the collection vessel connector (200) causing the dose control connector internal channel deformable elastomeric valve male end (314) and the collection vessel connector internal channel deformable elastomeric valve female end (216) to reverse bias and become sealed, thereby reversibly interrupting the fluid communication between the dose control connector internal channel (310) and the collection vessel connector internal channel (210); further comprises the act of reversing bias and becoming sealed creating a decreased pressure at the collection vessel connector female end fluid port (232), the decreased pressure withdrawing a fluid remaining on a surface of the collection vessel connector female end fluid port (232) into the collection vessel connector internal channel (210).

Similarly, the disengaging of the dose control connector (300) and the delivery control connector (500) thereby causing the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510), further comprises the act of reversing bias creating a decreased pressure at the delivery control connector female end fluid port (532), the decreased pressure withdrawing a fluid on the surface on a surface of the delivery control connector female end fluid port (532) into the delivery control connector internal channel (510). See FIGS. 6d-6e.

After detachment, the administrator or another person removes the connected dose control connector (300) and unit dose container (400) from the point of use and suitably transports the connected dose control connector (300) and unit dose container (400) to a point of disposal. Disposal of the apparatus (10) may be completed by removing the connected delivery site access device (600) and delivery control connector (500) from the delivery site (S) and suitably transporting the connected delivery site access device (600) and delivery control connector (500) for disposal. The connected dose control connector (300) and unit dose container (400) and the connected delivery site access device (600) and delivery control connector (500) may be suitably transported together or separately for disposal, and may also be transported to differing points of disposal, depending, or individual handling protocols.

At the point or points of disposal, personnel then suitably dispose of the dose control connector (300), the unit dose container (400), the delivery control connector (500), and the delivery site access device (600). It will be obvious to one skilled in the art that the pairs of apparatus (10) comprising the connected dose control connector (300) and unit dose container (400); and the connected delivery site access device (600) and delivery control connector (500), as seen in FIG. 11, will not generally need to be separated for disposal, thus minimizing the opportunities for contamination of the environment or of workers.

The method may be practiced in a large number of embodiments. By way of example only, and not limitation, it may be desired to have the dose control connector internal channel deformable elastomeric valve female end (316) reversibly sealing the dose control connector female end fluid port (334) from the environment, the dose control connector elastomeric valve female end (316) being biased in favor of being sealed. Therefore, in such an embodiment, the step of releasably interlocking the dose control connector female end fluid port interlock (334) to the unit dose container fluid port interlock (480) causes the dose control connector deformable elastomeric valve female end (316) to reverse bias and become opened.

In another embodiment, again by way of example only, and not limitation, it may be desired to have the delivery control connector deformable internal channel elastomeric valve male end (514) reversibly seal the delivery control connector male end fluid port (522) from the environment, the delivery control connector internal channel elastomeric valve male end (514) being biased in favor of being sealed. Therefore, in such an embodiment, the step of reversibly interlocking the delivery control connector male end fluid port interlock (524) to the delivery site access device female end fluid port interlock (634) causes the delivery control connector internal channel deformable elastomeric valve male end (514) to reverse bias and become opened.

In yet another embodiment, the act of releasably interlocking the collection vessel connector male end fluid port interlock (224) to the collection vessel fluid port interlock (180) may further comprise puncturing a collection vessel connector male end fluid port ingress means (223) through a collection vessel fluid port puncturable resealable elastomeric seal (174) in order to place the collection vessel male end fluid port (222) in fluid communication with the collection vessel volume (160). The method may involve connecting various interlock safety features, detailed above, in a compatible manner that prevents the apparatus (10) from accessing, or being accessed by, standard fluid handling devices. Examples are seen in FIGS. 12b-12c.

Furthermore, the method may include suitably transporting the connected dose control connector (300) and unit dose container (400) to a point of use in a closed container having an adsorbent inner layer and a moisture resistant outer layer, so that any leakage will be adsorbed by the inner layer for easy and safe disposal. For particular substances, such as by way of example only, radionuclides, suitably transporting the connected dose control connector (300) and unit dose container (400) to a point of use may further comprise enclosing the connected dose control connector (300) and unit dose container (400) in a radiation shielded container. Obviously, return of the apparatus (10) for disposal could be made using the same type of containers and precautions as are used for transporting of the apparatus (10) to the intended point of use.

The instant invention may also be practiced in embodiments in which one or more of the pieces of the apparatus (10) are permanently, rather than releasably attached, as detailed above. In one such embodiment, seen in FIGS. 13a and 13b, one or both of the pairs of the dose control connector (300) and the unit dose container (400); and the delivery control connector (500) and the delivery site access device (600), are permanently attached. Such a method may be also be described as being performed both by a "preparer" and an "administrator," although one skilled in the art will realize that such roles as exemplary only and may, in fact, be accomplished by one or more persons.

Such a method includes a preparer first enclosing a collection vessel volume (160) to be handled in a collection vessel (100) further comprising a collection vessel fluid port interlock (180), releasably interlockable to a collection vessel connector male end fluid port interlock (224). There is a collection vessel internal channel (110) in fluid communication with the collection vessel volume (160) and in fluid communication with a collection vessel fluid port (170) being reversibly sealed from the environment by a collection vessel fluid port elastomeric closure (172) being biased in favor of being sealed, as seen in other embodiments illustrated in FIGS. 1a-3d.

Next, the preparer releasably interlocks the collection vessel connector male end fluid port interlock (224) to the collection vessel fluid port interlock (180), thereby interlocking to the collection vessel (100) a collection vessel connector (200) having a connector vessel connector male end (220) and a collection vessel connector female end (230).

The connector vessel connector (200) further comprises the collection vessel connector male end fluid port interlock (224), a collection vessel connector male end fluid port (222) in fluid communication with a collection vessel connector internal channel (210), and a connection vessel connector female end fluid port (232) in fluid communication with the collection vessel connector internal channel (210). As seen in FIGS. 2a-2d, the collection vessel connector internal channel (210) contains a collection vessel connector internal channel deformable elastomeric valve (212) having a collection vessel connector internal channel deformable elastomeric valve male end (214) and a collection vessel connector internal channel deformable elastomeric valve female end (216).

The collection vessel connector internal channel deformable elastomeric valve female end (216) reversibly seals the collection vessel connector female end fluid port (232) from the collection vessel internal channel (210), and the collection vessel connector internal channel deformable elastomeric valve female end (216) is biased in favor of being sealed. There is additionally a collection vessel connector female end fluid port interlock (234).

The interlocking of the collection vessel connector (200) to the collection vessel (100) causes the collection vessel fluid port elastomeric closure (172) to reverse bias and become opened, thereby placing the collection vessel volume (160) in fluid communication with the collection vessel connector male end fluid port (222) and thereby in fluid communication with the collection vessel connector internal channel (210).

In this embodiment, the dose control connector female end fluid port interlock (334) is permanently attached to the unit dose container fluid port interlock (480), and thus, the two form an inseparable unit.

Figure 5:
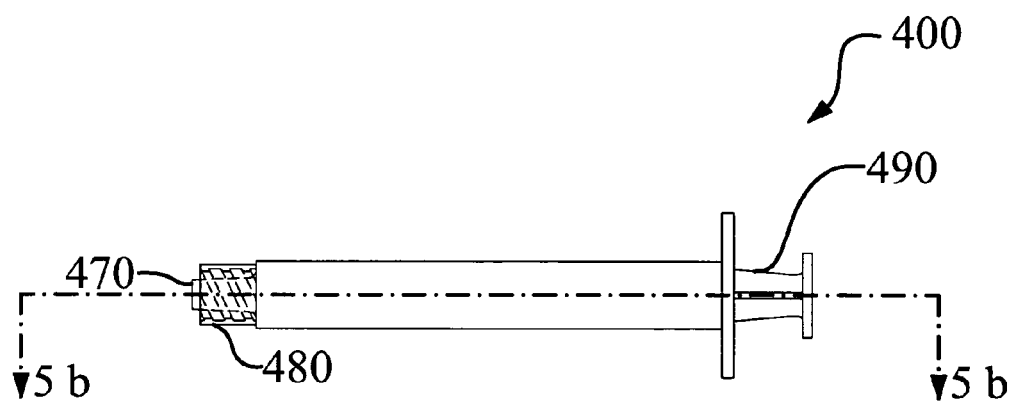
FIG. 5a is a side elevation view of an embodiment of a unit dose container (400) of the instant invention, not to scale.
FIG. 5b is a section view of an embodiment of the unit dose container (400) taken along section line 5b-5b in FIG. 5a, with the unit dose container manipulation regulator (490) partially withdrawn, not to scale.
Figure 5:
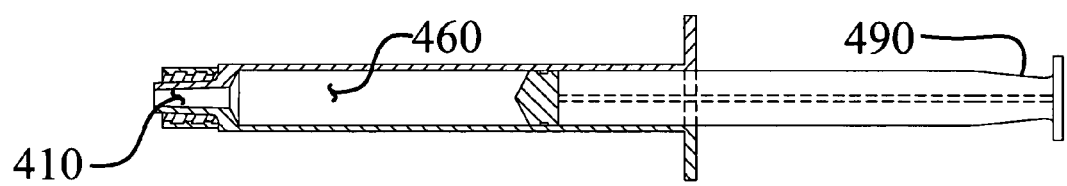

As seen in FIGS. 8a-8b and FIG. 5, the preparer then releasably interlocks a dose control connector male end fluid port interlock (324) to the collection vessel connector female end fluid port interlock (234), thereby interlocking to the collection vessel connector (200) a dose control connector (300) having a dose control connector male end (320) and a dose control connector female end (330). The dose control connector (300) further comprises the dose control connector male end fluid port interlock (324) and a dose control connector male end fluid port (322) in fluid communication with a dose control connector internal channel (310). The dose control connector internal channel (310) contains a dose control connector deformable elastomeric valve (312) having a dose control connector deformable elastomeric valve male end (314) and a dose control connector deformable elastomeric valve female end (316). The dose control connector deformable elastomeric valve male end (312) reversibly seals the dose control connector male end fluid port (322) from the environment, and the dose control connector elastomeric valve male end (312) is biased in favor of being sealed.

A dose control female end fluid port (332) is in fluid communication with the dose control connector internal channel (310); and a dose control connector female end fluid port interlock (334) permanently attaches the dose control connector (300) to the unit dose container fluid port interlock (480). The unit dose container (400) contains a unit dose container volume (460), and further comprises a unit dose container fluid port interlock (480) permanently interlocking the unit dose container (400) to the dose control connector (300), again as seen in FIG. 13a. A unit dose container internal channel (410) is in fluid communication with the unit dose container volume (460) and in fluid communication with a unit dose container fluid port (470) and a unit dose container fluid manipulation regulator (490) regulates the unit dose container volume (460). A unit dose container fluid port interlock (480) permanently attaches the unit dose container (400) to the dose control connector female end fluid port interlock (334).

The preparer then withdraws a predetermined amount of a hazardous fluid from the collection vessel (100) through the collection vessel connector (200) thence through the dose control connector (300), and thence into the unit dose container (400) by manipulation of the unit dose container fluid manipulation regulator (490), as seen in FIGS. 8a-8b.

The preparer next releasably detaches the dose control connector (300) from the collection vessel connector (200), the act of disengaging including the disengaging of the collection vessel connector female end fluid port interlock (234) and the dose control connector male end fluid port interlock (324), said disengaging causing the dose control connector internal channel deformable elastomeric valve male end (314) and the collection vessel connector internal channel deformable elastomeric valve female end (216) to reverse bias and become sealed, thereby interrupting the fluid communication between the dose control connector internal channel (310) and the collection vessel connector internal channel (210), as seen in FIGS. 2a-2d, FIGS. 4d-4e, and FIG. 8c.

The preparer or some other person then suitably transports the connected dose control connector (300) and unit dose container (400) to a point of use; whereupon the method will be employed by a person, called, by way of example only, the "administrator."

Also in this embodiment, the delivery site access device female end fluid port interlock (634) is permanently attached to delivery control connector male end fluid port interlock (534), and thus, the two form an inseparable unit.

The administrator first releasably attaches a delivery site access device (600) having a delivery site access device delivery site end (620) and a delivery site access device female end (630). The delivery site access device (600) further comprises a delivery site access device female end fluid port interlock (634); and a delivery site access device female end fluid port (632) in fluid communication with the delivery site access device internal channel (610), thence to the delivery site end fluid port (622), and thence to the delivery site (S). By way of example, and not limitation, a delivery site may be the lumen of a blood vessel.

The delivery site access device (600) has a delivery site access device delivery site end (620) having a delivery site connector delivery site end fluid port (622); and a delivery site access device female end (630) having a delivery site access device female end fluid port (632) in fluid communication with the delivery site connector internal channel (610). A delivery site access device female end fluid port interlock (634) permanently attaches the delivery site access device (600) to the delivery control connector male end fluid port interlock (524), as seen in FIG. 13b.

As seen in FIGS. 6a-6e, a delivery control connector (500) has a delivery control connector male end (520) and a delivery control connector female end (530) further comprising the delivery control connector male end fluid port interlock (524); and a delivery control connector male end fluid port (522) in fluid communication with a delivery control connector internal channel (510). The delivery control connector internal channel (510) contains a delivery control connector internal channel deformable elastomeric valve (512) having a delivery control connector internal channel deformable elastomeric valve male end (514) and a delivery control connector internal channel deformable elastomeric valve female end (516).

As seen in FIGS. 6a and 6d-6e, there is a delivery control connector female end fluid port (532) in fluid communication with the delivery control connector internal channel (510); wherein the delivery control connector internal channel deformable elastomeric valve female end (516) reversibly seals the delivery control connector female end fluid port (532) from the environment, and the delivery control connector internal channel elastomeric valve female end (516) is biased in favor of being sealed.

As seen in FIGS. 10 and 11, the administrator next releasably interlocks the dose control connector male end fluid port interlock (324) and the delivery control connector female end fluid port interlock (534), thereby interlocking the dose control connector (300) and the delivery control connector (500); said interlocking causing the dose control connector internal channel deformable elastomeric valve male end (314) and the delivery control connector internal channel deformable elastomeric valve female end (516) to reverse bias and become opened, and thereby to place the delivery control connector internal channel (510) and the dose control connector internal channel (310) in open fluid communication with the unit dose container volume (460).

The administrator may then dispense the hazardous fluid from the unit dose container (400) through the dose control connector (300) thence through the delivery control connector (500) and thence through the delivery site access device (600) to the delivery site (S) by means of manipulating the unit dose container fluid manipulation regulator.

Next, as seen in FIG. 11, the administrator releasably detaches the dose control connector (300) from the delivery control connector (500), the act of disengaging including the disengaging of dose control connector male end fluid port interlock (324) and the delivery control connector female end fluid port interlock (534) interlock, said disengaging causing the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510).

In suitable embodiments using appropriate connectors (200, 300, 500, and 600), detailed above, the method may be practiced such that the step of disengaging the dose control connector (300) and the collection vessel connector (200) thereby causing the dose control connector internal channel deformable elastomeric valve male end (314) and the collection vessel connector internal channel deformable elastomeric valve female end (216) to reverse bias and become sealed, thereby reversibly interrupting the fluid communication between the dose control connector internal channel (310) and the collection vessel connector internal channel (210); further comprises the act of reversing bias and becoming sealed creating a decreased pressure at the collection vessel connector female end fluid port (232), the decreased pressure withdrawing a fluid remaining on a surface of the collection vessel connector female end fluid port (232) into the collection vessel connector internal channel (210). Similarly, the disengaging of the dose control connector (300) and the delivery control connector (500) thereby causing the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510), further comprises the act of reversing bias creating a decreased pressure at the delivery control connector female end fluid port (532), the decreased pressure withdrawing a fluid on the surface on a surface of the delivery control connector female end fluid port (532) into the delivery control connector internal channel (510).

After detachment, the administrator or another person removes the permanently attached dose control connector (300) and unit dose container (400) from the point of use and suitably transports the permanently attached dose control connector (300) and unit dose container (400) to a point of disposal. Disposal of the apparatus (10) may be completed by removing the permanently attached delivery site access device (600) and delivery control connector (500) from the delivery site (S) and suitably transporting the permanently attached delivery site access device (600) and delivery control connector (500) to a point of disposal. The permanently attached dose control connector (300) and unit dose container (400); and the permanently attached delivery site access device (600) and delivery control connector (500) may be suitably transported together or separately to a point of disposal, and may also be transported to differing points of disposal, depending, or individual handling protocols.

At the point or points of disposal, personnel then suitably dispose of the dose control connector (300), the unit dose container (400), the delivery control connector (500), and the delivery site access device (600). It will be obvious to one skilled in the art that the permanently attached dose control connector (300) and unit dose container (400); and the permanently attached delivery site access device (600) and delivery control connector (500), as they appear by way of example in FIG. 11, need not, and if fact cannot, be separated for disposal, thus minimizing the opportunities for contamination of the environment or of workers.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims.

INDUSTRIAL APPLICABILITY

A method and apparatus for the handling of hazardous fluids answers a long felt need for handling a hazardous fluid, often, but not necessarily, in a medical setting, without employing connections based on the utilization of sharp needles to connect various pieces of fluid handling apparatus. Additionally, in some embodiments, the method and apparatus utilizes a deformable elastomeric valve that creates a decreased pressure at the surface of the valve, as the valve is closed, which withdraws any hazardous fluid remaining on the surface of the valve, into the apparatus, where it may be safely removed from an intended delivery site and disposed of in an appropriate manner.

I claim:

1. A method for the handling of a radiopharmaceutical fluid comprising the steps of:
   a) enclosing a collection vessel volume (160) to be handled in a collection vessel (100) further comprising:
      (i) a collection vessel fluid port interlock (180), releasably interlockable to a collection vessel connector male end fluid port interlock (224);
      (ii) a collection vessel internal channel (110) in fluid communication with the collection vessel volume (160) and in fluid communication with a collection vessel fluid port (170) being reversibly sealed from the environment by a collection vessel fluid port elastomeric closure (172) being biased in favor of being sealed;
   b) releasably interlocking the collection vessel connector male end fluid port interlock (224) to the collection vessel fluid port interlock (180), thereby interlocking to the collection vessel (100) a collection vessel connector (200) having a connector vessel connector male end (220) and a collection vessel connector female end (230) further comprising;
      i) the collection vessel connector male end fluid port interlock (224);

ii) a collection vessel connector male end fluid port (222) in fluid communication with a collection vessel connector internal channel (210);
iii) a connection vessel connector female end fluid port (232) in fluid communication with the collection vessel connector internal channel (210);
iv) the collection vessel connector internal channel (210) containing collection vessel connector internal channel deformable elastomeric valve (212) having a collection vessel connector internal channel deformable elastomeric valve male end (214) and a collection vessel connector internal channel deformable elastomeric valve female end (216);
v) wherein the collection vessel connector internal channel deformable elastomeric valve female end (216) reversibly seals the collection vessel connector female end fluid port (232) from the collection vessel internal channel (210), and the collection vessel connector internal channel deformable elastomeric valve female end (216) is biased in favor of being sealed;
vi) a collection vessel connector female end fluid port interlock (234); and said interlocking of the collection vessel connector male end fluid port interlock (224) to the collection vessel fluid port interlock (180) causing the collection vessel fluid port elastomeric closure (172) to reverse bias and become opened, thereby placing the collection vessel volume (160) in fluid communication with the collection vessel connector male end fluid port (222) and thereby in fluid communication with the collection vessel connector internal channel (210);
c) releasably interlocking a unit dose container male end fluid port interlock (480) to a dose control connector female end fluid port interlock (334), thereby interlocking to a dose control connector (300) a unit dose container (400) further comprising;
i) the unit dose container fluid port interlock (480);
ii) a unit dose container internal channel (410) in fluid communication with a unit dose container volume (460) and in fluid communication with a unit dose container fluid port (470); and
iii) a unit dose container fluid manipulation regulator (490) regulating the unit dose container volume (460); said interlocking of unit dose container fluid port interlock (480) and the dose control connector female end fluid port interlock (334) placing the unit dose connector internal channel (410), in fluid communication with the collection vessel connector internal channel (210);
d) releasably interlocking a dose control connector male end fluid port interlock (324) to the collection vessel connector female end fluid port interlock (234), thereby interlocking to the collection vessel connector (200) a dose control connector (300) having a dose control connector male end (320) and a dose control connector female end (330) further comprising;
i) the dose control connector male end fluid port interlock (324);
ii) a dose control connector male end fluid port (322) in fluid communication with a dose control connector internal channel (310);
iii) the dose control connector internal channel (310) containing a dose control connector deformable elastomeric valve (312) having a dose control connector deformable elastomeric valve male end (314) and a dose control connector deformable elastomeric valve female end (316);
iv) wherein the dose control connector deformable elastomeric valve male end (312) reversibly seals the dose control connector male end fluid port (322) from the environment, the dose control connector elastomeric valve male end (312) being biased in favor of being sealed;
v) a dose control female end fluid port (332) in fluid communication with the dose control connector internal channel (310);
vi) a dose control connector female end fluid port interlock (334); and said interlocking of the dose control connector male end fluid port interlock (324) to the collection vessel connector female end fluid port interlock (234), causing the collection vessel connector deformable elastomeric valve female end (216) and the dose control connector deformable elastomeric valve male end (314) to reverse bias and become opened, thereby placing the collection vessel volume (160) in fluid communication with the dose control connector male end fluid port (322) and thereby in fluid communication with the dose control connector internal channel (310);
e) withdrawing the radiopharmaceutical fluid from the collection vessel (100) through the collection vessel connector (200) thence through the dose control connector 300) and thence into the unit dose container (400) by manipulation of the unit dose container fluid manipulation regulator (490);
f) releasably disengaging the dose control connector (300) from the collection vessel connector (200), the act of disengaging including the disengaging of the collection vessel connector female end fluid port interlock (234) and the dose control connector male end fluid port interlock (324), said disengaging causing the dose control connector internal channel deformable elastomeric valve male end (314) and the collection vessel connector internal channel deformable elastomeric valve female end (216) to reverse bias and become sealed, thereby interrupting the fluid communication between the dose control connector internal channel (310) and the collection vessel connector internal channel (210);
g) suitably transporting the connected dose control connector (300) and unit dose container (400) to a point of use.

2. The method according to claim 1, further compromising the steps of:
a) releasably attaching a delivery site access device (600) having a delivery site connector delivery site end (620) and a delivery site access device delivery site end fluid port (622) to a delivery site (S), thereby interlocking to the delivery site (S) a delivery site access device (600) having a delivery site access device female end (630) further comprising:
i) a delivery site access device female end fluid port interlock (634);
ii) a delivery site access device female end fluid port (632) in fluid communication with a delivery site access device internal channel (610) thence to the delivery site end fluid port (622) and thence to the delivery site (S);
b) releasably interlocking a delivery control connector male end fluid port interlock (524) to the delivery site access device female end fluid port interlock (634), thereby interlocking to the delivery site (S) a delivery control connector (500) having a delivery control connector male end (520) and a delivery control connector female end (530) further comprising;
i) the delivery control connector male end fluid port interlock (524);
ii) a delivery control connector male end fluid port (522) in fluid communication with a delivery control connector internal channel (510);

iii) the delivery control connector internal channel (510) containing a delivery control connector internal channel deformable elastomeric valve (512) having a delivery control connector internal channel deformable elastomeric valve male end (514) and a delivery control connector internal channel deformable elastomeric valve female end (516);

iv) a delivery control connector female end fluid port (532) in fluid communication with the delivery control connector internal channel (510);

v) wherein the delivery control connector internal channel deformable elastomeric valve female end (516) reversibly seals the delivery control connector female end fluid port (532) from the environment, the delivery control connector internal channel elastomeric valve female end (516) being biased in favor of being sealed;

vi) said interlocking of the delivery control connector male end fluid port interlock (524) to the delivery site access device female end fluid port interlock (634) placing the delivery site (S) in fluid communication with the delivery site access device internal channel (610);

c) releasably interlocking the dose control connector male end fluid port interlock (324) and the delivery control connector female end fluid port interlock (534), thereby interlocking the dose control connector (300) and the delivery control connector (500); said interlocking of the dose control connector male end fluid port interlock (324) and the delivery control connector female end fluid port interlock (534), causing the dose control connector internal channel deformable elastomeric valve male end (314) and the delivery control connector internal channel deformable elastomeric valve female end (516) to reverse bias and become opened and thereby to place the delivery control connector internal channel (510) and the dose control connector internal channel (310) in fluid communication with the unit dose container volume (460);

d) dispensing the radiopharmaceutical fluid from the unit dose container (400) through the dose control connector (300) thence through the delivery control connector (500) and thence through the delivery site access device (600) to the delivery site (S) by means of manipulating the unit dose container fluid manipulation regulator (490); and e) releasably disengaging the dose control connector (300) from the delivery control connector (500), the act of disengaging including the disengaging of dose control connector male end fluid port interlock (324) and the delivery control connector female end fluid port interlock (534), said disengaging causing the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510).

3. The method according to claim 2, further comprising the steps of:
a) removing the dose control connector (300) and unit dose container (400) from the point of use and suitably transporting the dose control connector (300) and unit dose container (400) for disposal;
b) removing the delivery site access device (600) and delivery control connector (500) from the delivery site (S) and suitably transporting the connected delivery site access device (600) and delivery control connector (500) for disposal; and
c) suitably disposing of the dose control connector (300), the unit dose container (400), the delivery control connector (500), and the delivery site access device (600).

4. The method according to claim 2, wherein the dose control connector internal channel deformable elastomeric valve female end (316) reversibly seals the dose control connector female end fluid port (334) from the environment, the dose control connector elastomeric valve female end (316) being biased in favor of being sealed; and the step of releasably interlocking the dose control connector female end fluid port interlock (334) to the unit dose container fluid port interlock (480) causes the dose control connector deformable elastomeric valve female end (316) to reverse bias and become opened.

5. The method according to claim 2, wherein the delivery control connector deformable internal channel elastomeric valve male end (514) reversibly seals the delivery control connector male end fluid port (522) from the environment, the delivery control connector internal channel elastomeric valve male end (514) being biased in favor of being sealed; and the step of reversibly interlocking the delivery control connector male end fluid port interlock (524) to the delivery site access device female end fluid port interlock (634) causes the delivery control connector internal channel deformable elastomeric valve male end (514) to reverse bias and become opened.

6. The method according to claim 2, wherein the act of releasably interlocking the collection vessel connector male end fluid port interlock (224) to the collection vessel fluid port interlock (180) further comprises puncturing a collection vessel connector male end fluid port ingress regulator (223) through a collection vessel fluid port puncturable resealable elastomeric seal (174), thereby placing the collection vessel connector male end fluid port (222) in fluid communication with the collection vessel volume (160).

7. The method according to claim 2, wherein the collection vessel (100), the collection vessel connector (200), the dose control connector (300), the unit dose container (400), the delivery control connector (500), and the delivery site access device (600) are matched in coloration.

8. The method according to claim 2, wherein the act of releasably interlocking the collection vessel connector male end fluid port interlock (224) to the collection vessel fluid port interlock (180), further requires the engagement of a first interlock safety feature (555) on the collection vessel (100) and a cooperating second interlock safety feature (666) on the collection vessel connector (200).

9. The method according to claim 2, wherein the act of releasably interlocking a dose control connector male end fluid port interlock (324) to the collection vessel connector female end fluid port interlock (234), further requires the engagement of a third interlock safety feature (777) on the collection vessel connector (200) and a cooperating fourth interlock safety feature (888) on the dose control connector (300).

10. The method according to claim 2, wherein the act of releasably interlocking a unit dose container male end fluid port interlock (480) to the dose control connector fluid port interlock (334), further requires the engagement of a third interlock safety feature (777) on the dose control connector (300) and a cooperating fourth interlock safety feature (888) on the unit dose container (400).

11. The method according to claim 2, wherein the act of releasably disengaging the dose control connector (300) from the collection vessel connector (200), further requires the disengagement of a third interlock safety feature (777) on the collection vessel connector (200) and a cooperating fourth interlock safety feature (888) on the dose control connector (300).

12. The method according to claim 2, wherein the act of releasably interlocking a delivery control connector male end fluid port interlock (524) to the delivery site access device female end fluid port interlock (634), further requires the engagement of a third interlock safety feature (777) on the delivery site access device (600) and a cooperating fourth interlock safety feature (888) on the delivery control connector (500).

13. The method according to claim 2, wherein the act of releasably interlocking the dose control connector male end fluid port interlock (324) to the delivery control female end fluid port interlock (534), further requires the engagement of a third interlock safety feature (777) on the delivery control connector (500) and a cooperating fourth interlock safety feature (888) on the dose control connector (300).

14. The method according to claim 2, wherein the act of releasably disengaging the dose control connector (300) from the delivery control connector (500), further requires the disengagement of a third interlock safety feature (777) on the delivery control connector (500) and a cooperating fourth interlock safety feature (888) on the dose control connector.

15. The method according to claim 2, wherein the act of suitably transporting the connected dose control connector (300) and unit dose container (400) to a point of use further comprises enclosing the connected dose control connector (300) and unit dose container (400) in a closed container having an adsorbent inner layer and a moisture resistant outer layer.

16. The method according to claim 2, wherein the act of suitably transporting the connected dose control connector (300) and unit dose container (400) to a point of use further comprises enclosing the connected dose control connector (300) and unit dose container (400) in a radiation shielded container.

17. The method according to claim 2, wherein the step of disengaging the dose control connector (300) and the collection vessel connector (200) thereby causing the dose control connector internal channel deformable elastomeric valve male end (314) and the collection vessel connector internal channel deformable elastomeric valve female end (216) to reverse bias and become sealed, thereby reversibly interrupting the fluid communication between the dose control connector internal channel (310) and the collection vessel connector internal channel (210); further comprises the act of reversing bias and becoming sealed creating a decreased pressure at the collection vessel connector female end fluid port (232), the decreased pressure withdrawing substantially all of the fluid remaining on a surface of the collection vessel connector female end fluid port (232) into the collection vessel connector internal channel (210).

18. The method according to claim 2, wherein the step of disengaging the dose control connector (300) and the delivery control connector (500) causes the dose control connector internal channel deformable elastomeric valve male end (314) and the delivery control connector internal channel deformable elastomeric valve female end (516) to reverse bias and thereby to reversibly interrupt the fluid communication between the dose control connector internal channel (310) and the delivery control connector internal channel (510), further comprises the act of reversing bias creating a decreased pressure at the delivery control connector female end fluid port (532), the decreased pressure withdrawing substantially all of the fluid on the surface on a surface of the delivery control connector female end fluid port (532) into the delivery control connector internal channel (510).

19. An apparatus (10) for the handling of a radiopharmaceutical fluid comprising;
a) a collection vessel (100) containing a collection vessel volume (160), the collection vessel (100) further comprising:
  i) a collection vessel fluid port interlock (180), releasably attachable to a collection vessel connector (200);
  ii) a collection vessel internal channel (110) in fluid communication with the collection vessel volume (160) and in fluid communication with a collection vessel fluid port (170), being reversibly sealed from the environment by a collection vessel fluid port elastomeric closure (172) being biased in favor of being sealed; and
b) the collection vessel connector (200) further comprising;
  i) a collection vessel connector male end fluid port interlock (224) releasably interlocking the collection vessel connector (200) to the collection vessel (100);
  ii) a collection vessel connector male end fluid port (222) in fluid communication with a collection vessel connector internal channel (210);
  iii) a connection vessel connector female end fluid port (232) in fluid communication with the collection vessel connector internal channel (210);
  iv) the collection vessel connector internal channel (210) containing a collection vessel connector deformable elastomeric valve (212) having a collection vessel connector deformable elastomeric valve male end (214) and a collection vessel connector deformable elastomeric valve female end (216);
  v) wherein the collection vessel connector deformable elastomeric valve female end (216) reversibly seals the collection vessel female end fluid port (232) from the collection vessel internal channel (210), and the collection vessel connector elastomeric valve female end (216) is biased in favor of being sealed;
  vi) a collection vessel connector female end fluid port interlock (234) releasably interlocking the collection vessel connector (200) to a first external device selected from the group of first external devices consisting of a unit dose container (300), a dose control connector (400), a delivery control connector (500), and a delivery site access device (600);
c) the dose control connector (300) having;
  i) a dose control connector male end fluid port interlock (324) releasably interlocking the dose control connector (300) to a second external device selected from the group of second external devices consisting of the collection vessel connector (200), the delivery control connector (500), and the delivery site access device (600);
  ii) a dose control connector male end fluid port (322) in fluid communication with a dose control connector internal channel (310);
  iii) the dose control connector internal channel (310) containing a dose control connector deformable elastomeric valve (312) having a dose control connector deformable elastomeric valve male end (314) and a dose control connector deformable elastomeric valve female end (316);
  iv) wherein the dose control connector deformable elastomeric valve male end (312) reversibly seals the dose control male end fluid port (322) from the environment, the dose control connector elastomeric valve male end (312) being biased in favor of being sealed;

v) a dose control female end fluid port (332) in fluid communication with the dose control connector internal channel (310);

vi) a dose control connector female end fluid port interlock (334) releasably interlocking the dose control connector (300) to a third external device selected from the group of third external devices consisting of the unit dose container (400) and the delivery control connector (500);

d) the unit dose container (400) containing a unit dose container volume (460), the unit dose container (400) further comprising;

i) a unit dose container fluid port interlock (480) releasably interlocking the unit dose container (400) to a fourth external device selected from the group of fourth external devices consisting of the collection vessel connector (200), the dose control connector (300), the delivery control connector (500); and the delivery site access device (600);

ii) a unit dose container internal channel (410) in fluid communication with the unit dose container volume (460) and in fluid communication with a unit dose container fluid port (470);

iii) a unit dose container fluid manipulation regulator (490) regulating the unit dose container volume (460);

e) the delivery control connector (500) having;

i) a delivery control connector male end fluid port interlock (524) releasably interlocking the delivery control connector (500) to a fifth external device selected from the group of fifth external devices consisting of the collection vessel connector (200), the dose control connector (300), and the delivery site access device (600);

ii) a delivery control connector male end fluid port (522) in fluid communication with a delivery control connector internal channel (510);

iii) the delivery control connector internal channel (510) containing a delivery control connector deformable elastomeric valve (512) having a delivery control connector deformable elastomeric valve male end (514) and a delivery control connector deformable elastomeric valve female end (516);

iv) a delivery control female end fluid port (532) in fluid communication with the delivery control connector internal channel (510);

v) wherein the delivery control deformable elastomeric valve female end (516) reversibly seals the delivery control female end fluid port (532) from the environment, the delivery control connector elastomeric valve female end (516) being biased in favor of being sealed;

vi) a delivery control connector female end fluid port interlock (534) releasably interlocking the delivery control connector (500) to a sixth external device selected from the group of sixth external devices consisting of the unit dose container (400) and the dose control connector (300);

f) the delivery site access device (600) having;

i) a delivery site access device fluid port (632) in fluid communication with a delivery site access device internal channel (610) and thence to a delivery site (S);

ii) a delivery site interlock (630) releasably interlocking the delivery site connector to a seventh external device selected from the group of seventh external devices consisting of the unit dose container (400), the dose control connector (300), and the delivery control connector (500).

20. The apparatus (10) according to claim 19, wherein the dose control connector internal channel deformable elastomeric valve female end (316) reversibly seals the dose control female end fluid port (332) from the environment, the dose control connector elastomeric valve female end (316) being biased in favor of being sealed.

21. The apparatus (10) according to claim 19, wherein the delivery control connector deformable elastomeric valve male end (514) reversibly seals the delivery control male end fluid port (522) from the environment, the delivery control connector elastomeric valve male end (514) being biased in favor of being sealed.

22. The apparatus (10) according to claim 19, wherein the collection vessel fluid port elastomeric closure (172) further comprises a collection vessel fluid port puncturable resealable elastomeric seal (174).

23. The apparatus (10) according to claim 19, wherein the collection vessel connector male end fluid port (222) further comprises a collection vessel connector male end fluid port ingress regulator (223) capable of reversibly traversing the collection vessel fluid port puncturable resealable elastomeric seal (174) and thereby placing the collection vessel connector fluid port (222) in fluid communication with the collection vessel volume (160).

24. The apparatus (10) according to claim 19, wherein the collection vessel internal channel deformable elastomeric valve male end (214) is capable of sealing the collection vessel connector male end fluid port (222) from the environment, and the collection vessel internal channel deformable elastomeric valve male end (214) is biased in favor of being sealed.

25. The apparatus (10) according to claim 19, wherein the collection vessel fluid port interlock (180) further comprises a first interlock safety feature (555) capable of interlocking only with a cooperating second interlock safety feature (666) on the collection vessel connector (200).

26. The apparatus (10) according to claim 19, wherein the collection vessel connector female end fluid port interlock (234) further comprises a third interlock safety feature (777) capable of interlocking only with a cooperating fourth interlock safety feature (888).

27. The apparatus (10) according to claim 19, wherein the dose control connector female end fluid port interlock (434) further comprises a third interlock safety feature (777) capable of interlocking only with a cooperating fourth interlock safety feature (888).

28. The apparatus (10) according to claim 19, wherein the delivery control connector female end fluid port interlock (534) further comprises a third interlock safety feature (777) capable of interlocking only with a cooperating fourth interlock safety feature (888).

29. The apparatus (10) according to claim 19, wherein the delivery site access device interlock (630) further comprises a third interlock safety feature (777) capable of interlocking only with a cooperating fourth interlock safety feature (888).

30. The apparatus (10) according to claim 19, wherein the unit dose container fluid port interlock (480) further comprises a fourth interlock safety feature (888) capable of interlocking only with a cooperating third interlock safety feature (777).

31. The apparatus (10) according to claim 19, wherein the dose control connector male end fluid port interlock (324) further comprises a fourth interlock safety feature (888) capable of interlocking only with a mating third interlock safety feature (777).

32. The apparatus (10) according to claim 19, wherein the delivery control connector male end fluid port interlock (524) further comprises a fourth interlock safety feature (888) capable of interlocking only with a cooperating third interlock safety feature (777).

33. The apparatus (10) according to claim 19, wherein the delivery site access device interlock (630) further comprises a third interlock safety feature (777) capable of interlocking only with a mating fourth interlock safety feature (888).

34. The apparatus (10) according to claim 19, wherein the collection vessel (100), the collection vessel connector (200), the dose control connector (300), the unit does container (400), the delivery control connector (500), and the delivery site access device (600) are matched in coloration.

35. An apparatus (10) for the handling of a radiopharmaceutical fluid comprising;
 a) a collection vessel (100) containing a collection vessel volume (160), the collection vessel (100) further comprising:
  i) a collection vessel fluid port interlock (180), releasably attachable to a collection vessel connector (200);
  ii) a collection vessel internal channel (110) in fluid communication with the collection vessel volume (160) and in fluid communication with a collection vessel fluid port (170) reversibly sealed from the environment by a collection vessel fluid port elastomeric closure (172) being biased in favor of being sealed;
 b) the collection vessel connector (200) having a collection vessel male end (220) and a collection vessel female end (230) and further comprising;
  i) a collection vessel connector male end fluid port interlock (224) releasably interlocking the collection vessel connector (200) to the collection vessel (100);
  ii) a collection vessel connector male end fluid port (222) in fluid communication with a collection vessel connector internal channel (210);
  iii) a connection vessel connector female end fluid port (232) in fluid communication with the collection vessel connector internal channel (210);
  iv) the collection vessel connector internal channel (210) containing a collection vessel connector deformable elastomeric valve (212) having a collection vessel connector deformable elastomeric valve male end (214) and a collection vessel connector deformable elastomeric valve female end (216);
  v) wherein the collection vessel connector deformable elastomeric valve female end (216) reversibly seals the collection vessel female end fluid port (232) from the collection vessel internal channel (210), and the collection vessel connector elastomeric valve female end (216) is biased in favor of being sealed;
  vi) a collection vessel connector female end fluid port interlock (234) releasably interlocking the collection vessel connector (200) to a dose control connector (300);
 c) the dose control connector (300) having a dose control connector male end (320) and a dose control connector female end (330) and further comprising;
  i) a dose control connector male end fluid port interlock (324) releasably interlocking the dose control connector (300) to an eighth external device selected from the group of eighth external devices consisting of the collection vessel connector (200) and the delivery control connector (500);
  ii) a dose control connector male end fluid port (322) in fluid communication with a dose control connector internal channel (310);
  iii) the dose control connector internal channel (310) containing a dose control connector deformable elastomeric valve (312) having a dose control connector deformable elastomeric valve male end (314) and a dose control connector deformable elastomeric valve female end (316);
  iv) wherein the dose control connector deformable elastomeric valve male end (312) reversibly seals the dose control male end fluid port (322) from the environment, the dose control connector elastomeric valve male end (312) being biased in favor of being sealed;
  v) a dose control female end fluid port (332) in fluid communication with the dose control connector internal channel (310);
  vi) a dose control connector female end fluid port interlock (334) permanently interlocking the dose control connector (300) to the unit dose container fluid port interlock (480);
 d) the unit dose container (400) containing a unit dose container volume (460), the unit dose container (400) further comprising;
  i) a unit dose container fluid port interlock (480) permanently interlocking the unit dose container (400) to the dose control connector (300);
  ii) a unit dose container internal channel (410) in fluid communication with the unit dose container volume (460) and in fluid communication with a unit dose container fluid port (470);
  iii) a unit dose container fluid manipulation regulator (490) regulating the unit dose container volume (460);
  iv) a unit dose container fluid port interlock (480) permanently interlocking the unit dose container (400) to the dose control connector female end fluid port interlock (334);
 e) the delivery control connector (500) having a delivery control connector male end (520) and a delivery control connector female end (530) and further comprising;
  i) a delivery control connector male end fluid port interlock (524) permanently interlocking the delivery control connector (500) to the delivery site connector female end fluid port interlock (634);
  ii) a delivery control connector male end fluid port (522) in fluid communication with a delivery control connector internal channel (510);
  iii) the delivery control connector internal channel (510) containing a delivery control connector deformable elastomeric valve (512) having a delivery control connector deformable elastomeric valve male end (514) and a delivery control connector deformable elastomeric valve female end (516);
  iv) a delivery control female end fluid port (532) in fluid communication with the delivery control connector internal channel (510);
  v) wherein the delivery control deformable elastomeric valve female end (516) reversibly seals the delivery control female end fluid port (532) from the environment, the delivery control connector elastomeric valve female end (516) being biased in favor of being sealed;
  vi) a delivery control connector female end fluid port interlock (534) releasably interlocking the delivery control connector (500) the dose control connector (300);
 f) the delivery site access device (600) having a delivery site access device delivery site end (620) and a delivery site access device female end (630) and further comprises;
  i) a delivery site access device delivery site end (620) having delivery site connector delivery site end fluid port (622) in fluid communication with a delivery site access device internal channel (610);

ii) a delivery site access device female end (630) having a delivery site access device female end fluid port (632) in fluid communication with the delivery site connector internal channel (610); and iii) a delivery site access device female end fluid port interlock (634) permanently interlocking the delivery site access device (600) to the delivery control connector male end fluid port interlock (524).

\* \* \* \* \*